(12) United States Patent
Getman et al.

(10) Patent No.: US 9,663,829 B2
(45) Date of Patent: May 30, 2017

(54) COMPOSITIONS AND METHODS FOR DETECTING BV-ASSOCIATED BACTERIAL NUCLEIC ACID

(75) Inventors: Damon Kittredge Getman, Poway, CA (US); Paul M. Darby, San Diego, CA (US)

(73) Assignee: GEN-PROBE INCORPORATED, San Diego, CA (US)

( * ) Notice: Subject to any disclaimer, the term of this patent is extended or adjusted under 35 U.S.C. 154(b) by 93 days.

(21) Appl. No.: 14/343,701

(22) PCT Filed: Sep. 10, 2012

(86) PCT No.: PCT/US2012/054458
§ 371 (c)(1),
(2), (4) Date: May 15, 2014

(87) PCT Pub. No.: WO2013/036928
PCT Pub. Date: Mar. 14, 2013

(65) Prior Publication Data
US 2014/0302500 A1 Oct. 9, 2014

Related U.S. Application Data

(60) Provisional application No. 61/532,347, filed on Sep. 8, 2011.

(51) Int. Cl.
*C12Q 1/68* (2006.01)
*C07H 21/04* (2006.01)
*C12N 1/00* (2006.01)

(52) U.S. Cl.
CPC .......... *C12Q 1/689* (2013.01); *C12Q 1/6844* (2013.01); *C12Q 2600/118* (2013.01)

(58) Field of Classification Search
CPC . C12Q 1/6844; C12Q 1/689; C12Q 2600/118
See application file for complete search history.

(56) References Cited

U.S. PATENT DOCUMENTS

| | | | |
|---|---|---|---|
| 5,399,491 A * | 3/1995 | Kacian | C12Q 1/6855 435/6.1 |
| 5,654,418 A | 8/1997 | Sheiness et al. | |
| 7,625,704 B2 | 12/2009 | Fredricks et al. | |
| 2006/0046265 A1 | 3/2006 | Becker et al. | |
| 2007/0178495 A1 | 8/2007 | Fredricks et al. | |
| 2008/0305482 A1 | 12/2008 | Brentano et al. | |
| 2009/0291854 A1 | 11/2009 | Wiesinger-Mayr et al. | |
| 2009/0306230 A1 | 12/2009 | Semikhodskii et al. | |
| 2010/0075306 A1 | 3/2010 | Bretelle et al. | |
| 2011/0212852 A1 | 9/2011 | Getman | |

FOREIGN PATENT DOCUMENTS

| | | |
|---|---|---|
| JP | 2006129810 A | 5/2006 |
| WO | 2009123736 A2 | 10/2009 |
| WO | 2010/062001 A1 | 6/2010 |
| WO | 2011/027875 A1 | 3/2011 |
| WO | 2011/068679 A1 | 6/2011 |

OTHER PUBLICATIONS

Buck, G.A. et al., Biotechniques, vol. 27, pp. 528-536 (1999).*
Communication pursuant to Article 94(3) EPC, European Patent Application No. 12761858.5-1404, dated Jun. 15, 2015.
Balashov et al., "Identification, quantification and subtyping of Gardnerella vaginalis in noncultured clinical vaginal samples by quantitative PCR." J Med Microbiol. Feb. 2014, pp. 62-75., vol. 63(Pt 2):1, doi: 10.1099/jmm.0.066407-0. Epub Nov. 7, 2013. Abstract.
De Backer et al., "Quantitative determination by real-time PCR of four vaginal Lactobacillus species, Gardnerella vaginalis, and Atopobium vaginae indicates an inverse relationship between L. gasseri and L. iners," BMC Microbiology, Dec. 19, 2007, vol. 7, No. 115, doi:10.1186/1471-2180-7-115.
Fredricks et al., "Targeted PCR for Detection of Vaginal Bacteria Associated with Bacterial Vaginosis," Journal of Clinical Microbiology, Oct. 2007, p. 3270-3276, vol. 45, No. 10, doi:10.1128/JCM.01272-07, American Society for Microbiology.
Fredricks et al., "Molecular Identification of Bacteria Associated with Bacterial Vaginosis," N Engl J Med, Nov. 3, 2005, vol. 353, No. 18, pp. 1899-1911, Massachusetts Medical Society.
Menard et al, "Molecular Quantification of Gardnerella vaginalis and Atopobium vaginae Loads to Predict Bacterial Vaginosis," Clinical Infectious Diseases, 2008, vol. 47, pp. 33-43, doi:10.1086/588661, Infectious Diseases Society of America.
Muzny et al., "Gardnerella vaginalis: Still a Prime Suspect in the Pathogenesis of Bacterial Vaginosis," Curr. Infect. Dis Rep., Feb. 1, 2013, DOI 10.1007/s11908-013-0318-4, Springer Science+Business Media, New York.
Obata-Yasuoka et al., "A Multiplex Polymerase Chain Reaction—Based Diagnostic Method for Bacterial Vaginosis," Obstet Gynecol., Oct. 2002, vol. 100, No. 4, pp. 759-764, The American College of Obstetricians and Gynecologists. Published by Elsevier Science Inc.
Schwebke et al., "Role of Gadnerella vaginalis in the Pathogenesis of Bacterial Vaginosis—A Conceptual Model," Journal of Infectious Diseases Advance Access, Feb. 7, 2014, Published by Oxford University Press on behalf of the Infectious Diseases Society of America.
Schwebke et al., "Prevalence of Gardnerella vaginalis among women with lactobacillus-predominant vaginal flora," Sex Transm Infect, 2014, vol. 90, pp. 61-63, doi:10.1136/sextrans-2013-051232, Published by group.bmj.com.
Zariffard et al., "Detection of bacterial vaginosis-related organisms by real-time PCR for Lactobacilli, Gardnerella vaginalis and Mycoplasma hominis," FEMS Immunology and Medical Microbiology, 2002, vol. 34, pp. 277-281, Federation of European Microbiological Societies, published by Elsevier Science B.V.
Patent Examinational Report No. 1, Australian Patent Application No. 2012304327, mailed Oct. 9, 2014.

(Continued)

*Primary Examiner* — Teresa Strzelecka
(74) *Attorney, Agent, or Firm* — Jeffrey E. Landes; Nicholas V. Sherbina

(57) ABSTRACT

Disclosed are nucleic acid oligomers, including amplification oligomers, capture probes, and detection probes, for detection of a 16S rRNA or its encoding gene from bacterial species associated with bacterial vaginosis. Also disclosed are methods of specific nucleic acid amplification and detection using the disclosed oligomers, as well as corresponding reaction mixtures and kits.

16 Claims, 1 Drawing Sheet

(56) References Cited

OTHER PUBLICATIONS

International Search Report, International Patent Application No. PCT/US2012/054458, mailed Nov. 28, 2012.
Written Opinion, International Patent Application No. PCT/US2012/054458, mailed Nov. 28, 2012.
International Preliminary Report on Patentability, International Patent Application No. PCT/US2012/054458, issued Mar. 12, 2014.

* cited by examiner

```
TGGCGGCGTGCTTAACACATGCAAGTCGAACGGGATCTGACCAGCTTGCT
GGTTGGTGAGAGTGGCGAACGGGTGAGTAATGCGTGACCAACCTGCCCCA
TGCTCCAGAATAGCTCTTGGAAACGGGTGGTAATGCTGGATGCTCCAACT
TGACGCATGTCTTGTTGGGAAAGTGTTTAGTGGCATGGGATGGGGTCGCG
TCCTATCAGCTTGTAGGCGGGGTAATGGCCCACCTAGGCTTCGACGGGTA
GCCGGCCTGAGAGGGCGGACGGCCACATTGGGACTGAGATACGGCCCAGA
CTCCTACGGGAGGCAGCAGTGGGGAATATTGCGCAATGGGGGAAACCCTG
ACGCAGCGACGCCGCGTGCGGGATGAAGGCCTTCGGGTTGTAAACCGCTT
TTGATTGGGAGCAAGCCTTTTGGGTGAGTGTACCTTTCGAATAAGCGCCG
GCTAACTACGTGCCAGCAGCCGCGGTAATACGTAGGGCGCAAGCGTTATC
CGGAATTATTGGGCGTAAAGAGCTTGTAGGCGGTTCGTCGCGTCTGGTGT
GAAAGCCCATCGCTTAACGGTGGGTTTGCGCCGGGTACGGGCGGGCTAGA
GTGCAGTAGGGGAGACTGGAATTCTCGGTGTAACGGTGGAATGTGTAGAT
ATCGGGAAGAACACCAATGGCGAAGGCAGGTCTCTGGGCTGTTACTGACG
CTGAGAAGCGAAAGCGTGGGGAGCGAACAGGATTAGATACCCTGGTAGTC
CACGCCGTAAACGGTGGACGCTGGATGTGGGGCCCATTCCACGGGTTCTG
TGTCGGAGCTAACGCGTTAAGCGTCCCGCCTGGGGAGTACGGCCGCAAGG
CTAAAACTCAAAGAAATTGACGGGGGCCCGCACAAGCGGCGGAGCATGCG
GATTAATTCGATGCAACGCGAAGAACCTTACCTGGGCTTGACATGTGCCT
GACGACTGCAGAGATGTGGTTTCCTTTCGGGGCAGGTTCACAGGTGGTGC
ATGGTCGTCGTCAGCTCGTGTCGTGAGATGTTGGGTTAAGTCCCGCAACG
AGCGCAACCCTCGCCCTGTGTTGCCAGCGGGTTATGCCGGGAACTCACGG
GGGACCGCCGGGGTTAACTCGGAGGAAGGTGGGGATGACGTCAGATCATC
ATGCCCCTTACGTCCAGGGCTTCACGCATGCTACAATGGCCAGTACAACG
GGTTGYTTCATGGTGACATGGTGCTAATCCCTTAAAACTGGTCTCAGTTC
GGATCGTAGTCTGCAACTCGACTACGTGAAGGCGGAGTCGCTAGTAATCG
CGAATCAGCAACGTCGCGGTGAATGCGTTCCCGGGCCTTGTACACACCGC
CCGTCAAGTCATGAAAGTGGGCAGCACCCGAAGCCGGTGGCCTAACCCTT
TTGGGATGGAGCCGTCTAAGGTGAGGCTCGTGATTGGGACTAAGTCGTAA
CAAGGTAGCCGTA
```

COMPOSITIONS AND METHODS FOR DETECTING BV-ASSOCIATED BACTERIAL NUCLEIC ACID

CROSS REFERENCE TO RELATED APPLICATIONS

This application is a national stage entry of International Patent Application No. PCT/US2012/054458, filed Sep. 10, 2012, and claims the benefit of priority under 35 U.S.C. 119(e) to U.S. Provisional App. No. 61/532,347 filed Sep. 8, 2011, the contents of each are incorporated herein by reference in their entirety.

BACKGROUND OF THE INVENTION

Bacterial vaginosis (BV) is a common condition affecting millions of women annually that is associated with serious health problems such as preterm labor resulting in low birth weight, pelvic inflammatory disease, and increased risk of human immunodeficiency virus infection. See, e.g., Bodner-Adler et al., *Am. J. Obstet. Gynecol.* 189:139-47, 2003; Hillier et al., *Clin. Infect. Dis.* 20:Suppl 2:S276-S278, 1995; Peipert et al., *Am. J. Obstet. Gynecol.* 184:856-63, 2001; Hillier et al., *Am. J. Osbstet. Gynecol.* 175:435-41, 1996; Martin et al., *J. Infect. Dis.* 180:1863-1868, 1999; Sturm-Ramirez et al., *J. Infect. Dis.* 182:467-473, 2000. No single etiologic agent has been implicated as the cause of bacterial vaginosis, and the syndrome is currently considered to be a polymicrobial disorder that is characterized by depletion of vaginal *Lactobacillus* species that produce hydrogen peroxide and an increase in the quantity of several vaginal anaerobic bacteria. See, e.g., Eschenbach et al., *J. Clin. Microbiol.* 27:251-256, 1989; Fredricks et al., *J. Clin. Microbiol.* 47:721-726, 2009.

The more recent use of cultivation-independent analyses of 16S rRNA gene sequences has identified various, previously unrecognized species that are prevalent in the vaginal flora and appear to be associated with BV. See, e.g., Fredricks et al., *N. Engl. J. Med.* 353:1899-1911, 2005; Ferris et al., *J. Clin. Microbiol.* 45:1016-1018, 2007. Among these species are *Gardnerella vaginalis*. See, e.g., Fredricks et al., supra. Recent studies also suggest that *Gardnerella vaginalis* plays an important role in BV pathogenesis and may be a suitable marker of disease and treatment response. See Fredricks et al., *J. Clin. Microbiol.* 47:721-726, 2009.

Accordingly, there is a need for compositions, kits, and methods for rapidly and accurately detecting the presence or abundance of *Gardnerella vaginalis* in a specimen. Such compositions, kits, and methods would be particularly useful for the diagnosis of BV or for monitoring a patient's response to BV treatment. The present invention meets these and other needs.

SUMMARY OF THE INVENTION

In one aspect, the present invention provides a combination of at least two oligomers for detecting in a sample a *Gardnerella vaginalis* (GV) 16S rRNA or a gene encoding the GV 16S rRNA. Typically, the oligomer combination includes first and second amplification oligomers for amplifying a GV nucleic acid target region corresponding to the GV 16S rRNA or the 16S-rRNA-encoding gene. For example, in some embodiments, the first amplification oligomer comprises a first target-hybridizing sequence that is from about 15 to about 27 contiguous nucleotides contained in the sequence of SEQ ID NO:75 and that includes at least the sequence of at least one of SEQ ID NO:72 and SEQ ID NO:73, and the second amplification oligomer comprises a second target-hybridizing sequence that is from about 15 to about 27 contiguous nucleotides contained in the sequence of SEQ ID NO:71 and that includes at least the sequence of SEQ ID NO:70.

In certain embodiments of the oligomer combination, the first target-hybridizing sequence is selected from (a) a sequence contained in the sequence of SEQ ID NO:76 and optionally including at least the sequence of SEQ ID NO:72; (b) a sequence contained in the sequence of SEQ ID NO:78 and optionally including at least the sequence of SEQ ID NO:77; (c) a sequence contained in the sequence of SEQ ID NO:79 and optionally including at least the sequence of SEQ ID NO:73; and (d) a sequence contained in the sequence of SEQ ID NO:81 and optionally including at least the sequence of SEQ ID NO:80. Specific variations of a first target-hybridizing sequence as in (a)-(d) above include (a) the sequences shown in SEQ ID NO:6, SEQ ID NO:7, and SEQ ID NO:8; (b) the sequences shown in SEQ ID NO:7 and SEQ ID NO:8; (c) the sequences shown in SEQ ID NO:7, SEQ ID NO:8, SEQ ID NO:9, and SEQ ID NO:10; and (d) the sequences shown in SEQ ID NO:9 and SEQ ID NO:10.

In some embodiments of the oligomer combination, the second target-hybridizing sequence has a sequence selected from SEQ ID NO:35, SEQ ID NO:36, SEQ ID NO:37, SEQ ID NO:38, and SEQ ID NO:39. In other embodiments, the second target-hybridizing sequence is contained in the sequence of SEQ ID NO:86 and optionally includes at least the sequence of SEQ ID NO:85; specific variations of such a second target-hybridizing sequence include the sequences shown in SEQ ID NO:36, SEQ ID NO:38, and SEQ ID NO:39.

In some variations, the second amplification oligomer is a promoter primer or promoter provider further comprising a promoter sequence located 5' to the target-hybridizing sequence. Suitable promoter sequences include T7 RNA polymerase promoter sequences such as, e.g., the sequence shown in SEQ ID NO:87. In more specific embodiments, the second amplification oligomer has the sequence shown in SEQ ID NO:1, SEQ ID NO:2, SEQ ID NO:3, SEQ ID NO:4, or SEQ ID NO:5.

An oligomer combination may further include a terminating oligomer that hybridizes to a target sequence in the vicinity of the 5'-end of the GV nucleic acid target region. In some variations, a terminating oligomer has the sequence shown in SEQ ID NO:11, SEQ ID NO:12, SEQ ID NO:13, SEQ ID NO:14, SEQ ID NO:15, or SEQ ID NO:16.

An oligomer combination may also include at least one capture probe oligomer. In some such embodiments, the capture probe oligomer includes a target-hybridizing sequence covalently attached to a sequence or moiety that binds to an immobilized probe. Suitable target-hybridizing sequences include the sequences shown in SEQ ID NO:40, SEQ ID NO:41, SEQ ID NO:42, SEQ ID NO:43, SEQ ID NO:44, SEQ ID NO:45, and SEQ ID NO:46. In particular variations, the capture probe oligomer has a sequence selected from SEQ ID NO:25, SEQ ID NO:26, SEQ ID NO:27, SEQ ID NO:28, SEQ ID NO:29, SEQ ID NO:30, and SEQ ID NO:31.

In some embodiments, an oligomer combination further includes at least one detection probe oligomer. In particular embodiments, the detection probe oligomer includes a target-hybridizing sequence that is from about 14 to about 35 nucleotides in length and is configured to specifically hybridize to a target sequence contained within SEQ ID NO:88 from about nucleotide position 164 to about nucleotide position 205. In some such embodiments, the detection probe target-hybridizing sequence is contained in the sequence of SEQ ID NO:84 and includes at least the sequence of SEQ ID NO:83. In specific variations, the detection probe target-hybridizing sequence is selected from SEQ ID NO:20, SEQ ID NO:21, SEQ ID NO:22, SEQ ID NO:23, and SEQ ID NO:24.

In yet other embodiments, an oligomer combination further includes a pseudotarget oligomer that can be amplified using the first and second amplification oligomers. For example, in some variations wherein the first and second target-hybridizing sequences have the sequences shown, respectively, in SEQ ID NO:8 and SEQ ID NO:39, the pseudotarget oligomer has the sequence shown in SEQ ID NO:34.

In other aspects, the present invention provides a kit or a reaction mixture comprising an oligomer combination as above.

In yet another aspect, the present invention provides a method for detecting, in a sample, a *Gardnerella vaginalis* (GV) target nucleic acid, wherein the target nucleic acid is a GV 16S rRNA or a gene encoding the GV 16S rRNA. The method generally includes the following steps:
  (a) contacting a sample, suspected of containing a GV bacterium, with at least two oligomers for amplifying a GV nucleic acid target region corresponding to the target nucleic acid, the oligomer combination comprising (i) a first amplification oligomer comprising a first target-hybridizing sequence that is from about 15 to about 27 contiguous nucleotides contained in the sequence of SEQ ID NO:75 and that includes at least the sequence of at least one of SEQ ID NO:72 and SEQ ID NO:73, and (ii) a second amplification oligomer comprising a second target-hybridizing sequence that is from about 15 to about 27 contiguous nucleotides contained in the sequence of SEQ ID NO:71 and that includes at least the sequence of SEQ ID NO:70;
  (b) performing an in vitro nucleic acid amplification reaction, where any GV target nucleic acid present in said sample is used as a template for generating an amplification product; and
  (c) detecting the presence or absence of the amplification product, thereby indicating the presence or absence of GV in the sample.

In certain embodiments of the method, the first target-hybridizing sequence is selected from (a) a sequence contained in the sequence of SEQ ID NO:76 and optionally including at least the sequence of SEQ ID NO:72; (b) a sequence contained in the sequence of SEQ ID NO:78 and optionally including at least the sequence of SEQ ID NO:77; (c) a sequence contained in the sequence of SEQ ID NO:79 and optionally including at least the sequence of SEQ ID NO:73; and (d) a sequence contained in the sequence of SEQ ID NO:81 and optionally including at least the sequence of SEQ ID NO:80. Specific variations of a first target-hybridizing sequence as in (a)-(d) above include (a) the sequences shown in SEQ ID NO:6, SEQ ID NO:7, and SEQ ID NO:8; (b) the sequences shown in SEQ ID NO:7 and SEQ ID NO:8; (c) the sequences shown in SEQ ID NO:7, SEQ ID NO:8, SEQ ID NO:9, and SEQ ID NO:10; and (d) the sequences shown in SEQ ID NO:9 and SEQ ID NO:10.

In some embodiments of the method, the second target-hybridizing sequence has a sequence selected from SEQ ID NO:35, SEQ ID NO:36, SEQ ID NO:37, SEQ ID NO:38, and SEQ ID NO:39. In other embodiments, the second target-hybridizing is contained in the sequence of SEQ ID NO:86 and optionally includes at least the sequence of SEQ ID NO:85; specific variations of such a second target-hybridizing sequence include the sequences shown in SEQ ID NO:36, SEQ ID NO:38, and SEQ ID NO:39.

In some variations of the method, the second amplification oligomer is a promoter primer or promoter provider further comprising a promoter sequence located 5' to the target-hybridizing sequence. Suitable promoter sequences include T7 RNA polymerase promoter sequences such as, e.g., the sequence shown in SEQ ID NO:87. In more specific embodiments, the second amplification oligomer has the sequence shown in SEQ ID NO:1, SEQ ID NO:2, SEQ ID NO:3, SEQ ID NO:4, or SEQ ID NO:5.

Typically, the method for detecting the *G. vaginalis* target nucleic acid further comprising purifying the GV target nucleic acid from other components in the sample before the amplification step (a). In particular embodiments, the purifying step includes contacting the sample with at least one capture probe oligomer comprising a target-hybridizing sequence covalently attached to a sequence or moiety that binds to an immobilized probe. Suitable target-hybridizing sequences include the sequences shown in SEQ ID NO:40, SEQ ID NO:41, SEQ ID NO:42, SEQ ID NO:43, SEQ ID NO:44, SEQ ID NO:45, and SEQ ID NO:46. In particular variations, the capture probe oligomer has a sequence selected from SEQ ID NO:25, SEQ ID NO:26, SEQ ID NO:27, SEQ ID NO:28, SEQ ID NO:29, SEQ ID NO:30, and SEQ ID NO:31.

In some embodiments, the detecting step (c) includes contacting the in vitro nucleic acid amplification reaction with a detection probe oligomer configured to specifically hybridize to the amplification product under conditions whereby the presence or absence of the amplification product is determined, thereby indicating the presence or absence of GV in the sample. In particular embodiments, the detection probe oligomer includes a target-hybridizing sequence that is from about 14 to about 35 nucleotides in length and is configured to specifically hybridize to a target sequence contained within SEQ ID NO:88 from about nucleotide position 164 to about nucleotide position 205. In some such embodiments, the detection probe target-hybridizing sequence is contained in the sequence of SEQ ID NO:84 and includes at least the sequence of SEQ ID NO:83. In specific variations, the detection probe target-hybridizing sequence is selected from SEQ ID NO:20, SEQ ID NO:21, SEQ ID NO:22, SEQ ID NO:23, and SEQ ID NO:24.

In some embodiments of a method utilizing a detection probe oligomer, the detection probe includes at least one label. In specific variations, the one or more label(s) are selected from a chemiluminescent label, a fluorescent label, a quencher, or any combination thereof.

In other embodiments of a method utilizing a detection probe oligomer, the detecting step (c) occurs during the amplifying step (b). In some such embodiments, the detection probe comprises a fluorescent label, a quencher, or both (e.g., a TaqMan detection probe or a molecular beacon).

In still other embodiments of a method utilizing a detection probe oligomer, the detection probe further comprises a non-target-hybridizing sequence. In particular embodiments, the detection probe comprising a non-target-hybridizing sequence is a hairpin detection probe such as, e.g., a molecular beacon or a molecular torch.

In certain embodiments of the method for detecting the GV target nucleic acid, the amplification reaction at step (b) is an isothermal amplification reaction or a PCR amplification reaction. In specific variations, the isothermal amplification reaction is a transcription-mediated amplification (TMA) reaction (e.g., a reverse TMA reaction). In some embodiments of a method utilizing an isothermal or PCR amplification reaction, the reaction is a real-time amplification reaction.

In yet other embodiments, the method for detecting the GV target nucleic acid further includes contacting the sample with a pseudotarget oligomer that can be amplified, using the first and second amplification oligomers, in the in vitro nucleic acid amplification reaction to generate a second amplification product that does not specifically hybridize to the detection probe under the detection reaction conditions. For example, in some variations wherein the first and second target-hybridizing sequences have the sequences shown, respectively, in SEQ ID NO:8 and SEQ ID NO:39, the sample is contacted with a pseudotarget oligomer having the sequence shown in SEQ ID NO:34.

In still another aspect, the present invention provides a detection probe oligomer for detecting a *Gardnerella vaginalis* target nucleic acid. In some embodiments, the detection probe oligomer comprises a target-hybridizing sequence that is from about 14 to about 35 nucleotides in length and is configured to specifically hybridize to a target sequence contained within SEQ ID NO:88 from about nucleotide position 164 to about nucleotide position 205. In some such embodiments, the detection probe target-hybridizing sequence is contained in the sequence of SEQ ID NO:84 and includes at least the sequence of SEQ ID NO:83. In specific variations, the detection probe target-hybridizing sequence is selected from SEQ ID NO:20, SEQ ID NO:21, SEQ ID NO:22, SEQ ID NO:23, and SEQ ID NO:24.

In some embodiments of a detection probe oligomer, the detection probe includes at least one label. In specific variations, the one or more label(s) are selected from a chemiluminescent label, a fluorescent label, a quencher, or any combination thereof. In more specific variations, the detection probe comprises a fluorescent label and a quencher (e.g., a TaqMan detection probe or a molecular beacon).

In other embodiments of a detection probe oligomer, the detection probe further comprises a non-target-hybridizing sequence. In particular variations, the detection probe comprising a non-target-hybridizing sequence is a hairpin detection probe such as, e.g., a molecular beacon or a molecular torch.

These and other aspects of the invention will become evident upon reference to the following detailed description of the invention and the attached drawings.

DEFINITIONS

Unless defined otherwise, all technical and scientific terms used herein have the same meaning as commonly understood by one of ordinary skill in the art pertinent to the methods and compositions described. As used herein, the following terms and phrases have the meanings ascribed to them unless specified otherwise.

The terms "a," "an," and "the" include plural referents, unless the context clearly indicates otherwise. For example, "a nucleic acid" as used herein is understood to represent one or more nucleic acids. As such, the terms "a" (or "an"), "one or more," and "at least one" can be used interchangeably herein.

"Sample" includes any specimen that may contain *Gardnerella vaginalis* or components thereof, such as nucleic acids or fragments of nucleic acids. Samples include "biological samples" which include any tissue or material derived from a living or dead human that may contain *G. vaginalis* or target nucleic acid derived therefrom, including, e.g., vaginal swab samples, cervical brush samples, respiratory tissue or exudates such as bronchoscopy, bronchoalveolar lavage (BAL) or lung biopsy, sputum, saliva, peripheral blood, plasma, serum, lymph node, gastrointestinal tissue, feces, urine, semen or other body fluids or materials. The biological sample may be treated to physically or mechanically disrupt tissue or cell structure, thus releasing intracellular components into a solution which may further contain enzymes, buffers, salts, detergents and the like, which are used to prepare, using standard methods, a biological sample for analysis. Also, samples may include processed samples, such as those obtained from passing samples over or through a filtering device, or following centrifugation, or by adherence to a medium, matrix, or support.

"Nucleic acid" refers to a multimeric compound comprising two or more covalently bonded nucleosides or nucleoside analogs having nitrogenous heterocyclic bases, or base analogs, where the nucleosides are linked together by phosphodiester bonds or other linkages to form a polynucleotide. Nucleic acids include RNA, DNA, or chimeric DNA-RNA polymers or oligonucleotides, and analogs thereof. A nucleic acid "backbone" may be made up of a variety of linkages, including one or more of sugar-phosphodiester linkages, peptide-nucleic acid bonds (in "peptide nucleic acids" or PNAs, see, e.g., International Patent Application Pub. No. WO 95/32305), phosphorothioate linkages, methylphosphonate linkages, or combinations thereof. Sugar moieties of the nucleic acid may be either ribose or deoxyribose, or similar compounds having known substitutions such as, for example, 2'-methoxy substitutions and 2'-halide substitutions (e.g., 2'-F). Nitrogenous bases may be conventional bases (A, G, C, T, U), analogs thereof (e.g., inosine, 5-methylisocytosine, isoguanine; see, e.g., *The Biochemistry of the Nucleic Acids* 5-36, Adams et al., ed., 11th ed., 1992; Abraham et al., 2007, *BioTechniques* 43: 617-24), which include derivatives of purine or pyrimidine bases (e.g., $N^4$-methyl deoxygaunosine, deaza- or aza-purines, deaza- or aza-pyrimidines, pyrimidine bases having substituent groups at the 5 or 6 position, purine bases having an altered or replacement substituent at the 2, 6 and/or 8 position, such as 2-amino-6-methylaminopurine, $O^6$-methylguanine, 4-thio-pyrimidines, 4-amino-pyrimidines, 4-dimethylhydrazine-pyrimidines, and $O^4$-alkyl-pyrimidines, and pyrazolo-compounds, such as unsubstituted or 3-substituted pyrazolo [3,4-d]pyrimidine; U.S. Pat. Nos. 5,378,825, 6,949,367 and International Patent Application Pub. No. WO 93/13121, each incorporated by reference herein). Nucleic acids may include "abasic" residues in which the backbone does not include a nitrogenous base for one or more residues (see, e.g., U.S. Pat. No. 5,585,481, incorporated by reference herein). A nucleic acid may comprise only conventional sugars, bases, and linkages as found in RNA and DNA, or may include conventional components and substitutions (e.g., conventional bases linked by a 2'-methoxy backbone, or a nucleic acid including a mixture of conventional bases and one or more base analogs). Nucleic acids may include "locked nucleic acids" (LNA), in which one or more nucleotide monomers have a bicyclic furanose unit locked in an RNA mimicking sugar conformation, which enhances hybridization affinity toward complementary sequences in single-stranded RNA (ssRNA), single-stranded DNA (ssDNA), or double-stranded DNA (dsDNA) (Vester et al., *Biochemistry* 43:13233-41, 2004, incorporated by reference herein). Nucleic acids may include modified bases to alter the function or behavior of the nucleic acid, e.g., addition of a 3'-terminal dideoxynucleotide to block additional nucleotides from being added to the nucleic acid. Synthetic methods for making nucleic acids in vitro are well known in the art although nucleic acids may be purified from natural sources using routine techniques.

The term "polynucleotide" as used herein denotes a nucleic acid chain. Throughout this application, nucleic acids are designated by the 5'-terminus to the 3'-terminus. Standard nucleic acids, e.g., DNA and RNA, are typically synthesized "3'-to-5'," i.e., by the addition of nucleotides to the 5'-terminus of a growing nucleic acid.

A "nucleotide" as used herein is a subunit of a nucleic acid consisting of a phosphate group, a 5-carbon sugar and a nitrogenous base. The 5-carbon sugar found in RNA is ribose. In DNA, the 5-carbon sugar is 2'-deoxyribose. The term also includes analogs of such subunits, such as a methoxy group at the 2' position of the ribose (2'-O-Me). As used herein, methoxy oligonucleotides containing "T" residues have a methoxy group at the 2' position of the ribose moiety, and a uracil at the base position of the nucleotide.

A "non-nucleotide unit" as used herein is a unit that does not significantly participate in hybridization of a polymer. Such units must not, for example, participate in any significant hydrogen bonding with a nucleotide, and would exclude units having as a component one of the five nucleotide bases or analogs thereof.

A "target nucleic acid" as used herein is a nucleic acid comprising a target sequence to be amplified. Target nucleic acids may be DNA or RNA as described herein, and may be either single-stranded or double-stranded. The target nucleic acid may include other sequences besides the target sequence, which may not be amplified. Typical target nucleic acids include virus genomes, bacterial genomes, fungal genomes, plant genomes, animal genomes, rRNA, tRNA, or mRNA from viruses, bacteria or eukaryotic cells, mitochondrial DNA, or chromosomal DNA.

By "isolated" it is meant that a sample containing a target nucleic acid is taken from its natural milieu, but the term does not connote any degree of purification.

The term "target sequence" as used herein refers to the particular nucleotide sequence of the target nucleic acid that is to be amplified and/or detected. The "target sequence" includes the complexing sequences to which oligonucleotides (e.g., priming oligonucleotides and/or promoter oligonucleotides) complex during an amplification processes (e.g., TMA). Where the target nucleic acid is originally single-stranded, the term "target sequence" will also refer to the sequence complementary to the "target sequence" as present in the target nucleic acid. Where the target nucleic acid is originally double-stranded, the term "target sequence" refers to both the sense (+) and antisense (−) strands. In choosing a target sequence, the skilled artisan will understand that a "unique" sequence should be chosen so as to distinguish between unrelated or closely related target nucleic acids.

"Target-hybridizing sequence" is used herein to refer to the portion of an oligomer that is configured to hybridize with a target nucleic acid sequence. Preferably, the target-hybridizing sequences are configured to specifically hybridize with a target nucleic acid sequence. Target-hybridizing sequences may be 100% complementary to the portion of the target sequence to which they are configured to hybridize; but not necessarily. Target-hybridizing sequences may also include inserted, deleted and/or substituted nucleotide residues relative to a target sequence. Less than 100% complementarity of a target-hybridizing sequence to a target sequence may arise, for example, when the target nucleic acid is a plurality strains within a species, such as would be the case for an oligomer configured to hybridize to the various strains of *G. vaginalis*. It is understood that other reasons exist for configuring a target-hybridizing sequence to have less than 100% complementarity to a target nucleic acid.

Oligomer target-hybridizing sequences defined herein by reference to a specific sequence (e.g., by reference a region within SEQ ID NO:45) are also understood to include functional complements thereof, unless the context clearly dictates otherwise. Thus, for example, where target-hybridizing regions of first and second amplification oligomers are defined by reference to specific sequences corresponding, respectively, to sense and antisense strands of a target nucleic acid, it is understood that the amplification oligomer combination may include a functional combination of first and second amplification oligomers having target-hybridizing sequences that are the respective complements of the specific reference sequences. Similarly, and again by way of example, where a target-hybridizing sequence for a detection probe oligomer is defined reference to a specific sequence, it is understood that the detection probe may include a corresponding detection probe oligomer having a target-hybridizing sequence that is the complement of the specific reference sequence; or where a detection probe oligomer is defined by its configuration to hybridize to a specific sequence, it is understood that the detection probe may include a corresponding detection probe oligomer having a target-hybridizing sequence that is configured to hybridize to the complement of the specific reference sequence.

The term "targets a sequence" as used herein in reference to a region of *Gardnerella vaginalis* (GV) nucleic acid refers to a process whereby an oligonucleotide hybridizes to the target sequence in a manner that allows for amplification and detection as described herein. In one preferred embodiment, the oligonucleotide is complementary with the targeted GV nucleic acid sequence and contains no mismatches. In another preferred embodiment, the oligonucleotide is complementary but contains 1, 2, 3, 4, or 5 mismatches with the targeted GV nucleic acid sequence. Preferably, the oligonucleotide that hybridizes to the GV nucleic acid sequence includes at least 10 to as many as 50 nucleotides complementary to the target sequence. It is understood that at least 10 and as many as 50 is an inclusive range such that 10, 50 and each whole number there between are included. Preferably, the oligomer specifically hybridizes to the target sequence.

The term "configured to" denotes an actual arrangement of the polynucleotide sequence configuration of a referenced oligonucleotide target-hybridizing sequence. For example, amplification oligomers that are configured to generate a specified amplicon from a target sequence have polynucleotide sequences that hybridize to the target sequence and can be used in an amplification reaction to generate the amplicon. Also as an example, oligonucleotides that are configured to specifically hybridize to a target sequence have a polynucleotide sequence that specifically hybridizes to the referenced sequence under stringent hybridization conditions.

The term "configured to specifically hybridize to" as used herein means that the target-hybridizing region of an amplification oligonucleotide, detection probe, or other oligonucleotide is designed to have a polynucleotide sequence that could target a sequence of the referenced *Gardnerella vaginalis* (GV) target region. Such an oligonucleotide is not limited to targeting that sequence only, but is rather useful as a composition, in a kit or in a method for targeting a GV target nucleic acid. The oligonucleotide is designed to function as a component of an assay for amplification and detection of GV from a sample, and therefore is designed to target GV in the presence of other nucleic acids commonly found in testing samples. "Specifically hybridize to" does not mean exclusively hybridize to, as some small level of hybridization to non-target nucleic acids may occur, as is understood in the art. Rather, "specifically hybridize to" means that the oligonucleotide is configured to function in an assay to primarily hybridize the target so that an accurate detection of target nucleic acid in a sample can be determined. The term "configured to" denotes an actual arrangement of the polynucleotide sequence configuration of the amplification oligonucleotide target-hybridizing sequence.

The term "fragment," as used herein in reference to the *Gardnerella vaginalis* targeted nucleic acid, refers to a piece of contiguous nucleic acid. In certain embodiments, the fragment includes contiguous nucleotides from a *Gardnerella vaginalis* 16S ribosomal RNA, wherein the number of 16S contiguous nucleotides in the fragment are less than that for the entire 16S.

The term "region," as used herein, refers to a portion of a nucleic acid wherein said portion is smaller than the entire nucleic acid. For example, when the nucleic acid in reference is an oligonucleotide promoter primer, the term "region" may be used refer to the smaller promoter portion of the entire oligonucleotide. Similarly, and also as example only, when the nucleic acid is a 16S ribosomal RNA, the term "region" may be used to refer to a smaller area of the nucleic acid, wherein the smaller area is targeted by one or more oligonucleotides of the invention. As another non-limiting example, when the nucleic acid in reference is an amplicon, the term region may be used to refer to the smaller nucleotide sequence identified for hybridization by the target-hybridizing sequence of a probe.

The interchangeable terms "oligomer," "oligo," and "oligonucleotide" refer to a nucleic acid having generally less than 1,000 nucleotide (nt) residues, including polymers in a range having a lower limit of about 5 nt residues and an upper limit of about 500 to 900 nt residues. In some embodiments, oligonucleotides are in a size range having a lower limit of about 12 to 15 nt and an upper limit of about 50 to 600 nt, and other embodiments are in a range having a lower limit of about 15 to 20 nt and an upper limit of about 22 to 100 nt. Oligonucleotides may be purified from naturally occurring sources or may be synthesized using any of a variety of well-known enzymatic or chemical methods. The term oligonucleotide does not denote any particular function to the reagent; rather, it is used generically to cover all such reagents described herein. An oligonucleotide may serve various different functions. For example, it may function as a primer if it is specific for and capable of hybridizing to a complementary strand and can further be extended in the presence of a nucleic acid polymerase; it may function as a primer and provide a promoter if it contains a sequence recognized by an RNA polymerase and allows for transcription (e.g., a T7 Primer); and it may function to detect a target nucleic acid if it is capable of hybridizing to the target nucleic acid, or an amplicon thereof, and further provides a detectable moiety (e.g., an acridinium-ester compound).

As used herein, an oligonucleotide "substantially corresponding to" a specified reference nucleic acid sequence means that the oligonucleotide is sufficiently similar to the reference nucleic acid sequence such that the oligonucleotide has similar hybridization properties to the reference nucleic acid sequence in that it would hybridize with the same target nucleic acid sequence under stringent hybridization conditions. One skilled in the art will understand that "substantially corresponding oligonucleotides" can vary from a reference sequence and still hybridize to the same target nucleic acid sequence. It is also understood that a first nucleic acid corresponding to a second nucleic acid includes the RNA and DNA thereof and includes the complements thereof, unless the context clearly dictates otherwise. This variation from the nucleic acid may be stated in terms of a percentage of identical bases within the sequence or the percentage of perfectly complementary bases between the probe or primer and its target sequence. Thus, in certain embodiments, an oligonucleotide "substantially corresponds" to a reference nucleic acid sequence if these percentages of base identity or complementarity are from 100% to about 80%. In preferred embodiments, the percentage is from 100% to about 85%. In more preferred embodiments, this percentage is from 100% to about 90%; in other preferred embodiments, this percentage is from 100% to about 95%. Similarly, a region of a nucleic acid or amplified nucleic acid can be referred to herein as corresponding to a reference nucleic acid sequence. One skilled in the art will understand the various modifications to the hybridization conditions that might be required at various percentages of complementarity to allow hybridization to a specific target sequence without causing an unacceptable level of non-specific hybridization.

A "helper oligonucleotide" or "helper" refers to an oligonucleotide designed to bind to a target nucleic acid and impose a different secondary and/or tertiary structure on the target to increase the rate and extent of hybridization of a detection probe or other oligonucleotide with the targeted nucleic acid, as described, for example, in U.S. Pat. No. 5,030,557, incorporated by reference herein. Helpers may also be used to assist with the target hybridization and function of primer, target capture and other oligonucleotides.

As used herein, a "blocking moiety" is a substance used to "block" the 3'-terminus of an oligonucleotide or other nucleic acid so that it cannot be efficiently extended by a nucleic acid polymerase. Oligomers not intended for extension by a nucleic acid polymerase may include a blocker group that replaces the 3' OH to prevent enzyme-mediated extension of the oligomer in an amplification reaction. For example, blocked amplification oligomers and/or detection probes present during amplification may not have functional 3' OH and instead include one or more blocking groups located at or near the 3' end. In some embodiments a blocking group near the 3' end and may be within five residues of the 3' end and is sufficiently large to limit binding of a polymerase to the oligomer. In other embodiments a blocking group is covalently attached to the 3' terminus. Many different chemical groups may be used to block the 3' end, e.g., alkyl groups, non-nucleotide linkers, alkane-diol dideoxynucleotide residues, and cordycepin.

An "amplification oligomer" is an oligomer, at least the 3'-end of which is complementary to a target nucleic acid, and which hybridizes to a target nucleic acid, or its complement, and participates in a nucleic acid amplification reaction. An example of an amplification oligomer is a "primer" that hybridizes to a target nucleic acid and contains a 3' OH end that is extended by a polymerase in an amplification process. Another example of an amplification oligomer is an oligomer that is not extended by a polymerase (e.g., because it has a 3' blocked end) but participates in or facilitates amplification. For example, the 5' region of an amplification oligonucleotide may include a promoter sequence that is non-complementary to the target nucleic acid (which may be referred to as a "promoter primer" or "promoter provider").

Those skilled in the art will understand that an amplification oligomer that functions as a primer may be modified to include a 5' promoter sequence, and thus function as a promoter primer. Incorporating a 3' blocked end further modifies the promoter primer, which is now capable of hybridizing to a target nucleic acid and providing an upstream promoter sequence that serves to initiate transcription, but does not provide a primer for oligo extension. Such a modified oligo is referred to herein as a "promoter provider" oligomer. Size ranges for amplification oligonucleotides include those that are about 10 to about 70 nt long (not including any promoter sequence or poly-A tails) and contain at least about 10 contiguous bases, or even at least 12 contiguous bases that are complementary to a region of the target nucleic acid sequence (or a complementary strand thereof). The contiguous bases are at least 80%, or at least 90%, or completely complementary to the target sequence to which the amplification oligomer binds. An amplification oligomer may optionally include modified nucleotides or analogs, or additional nucleotides that participate in an amplification reaction but are not complementary to or contained in the target nucleic acid, or template sequence. It is understood that when referring to ranges for the length of an oligonucleotide, amplicon, or other nucleic acid, that the range is inclusive of all whole numbers (e.g., 19-25 contiguous nucleotides in length includes 19, 20, 21, 22, 23, 24 & 25).

As used herein, a "promoter" is a specific nucleic acid sequence that is recognized by a DNA-dependent RNA polymerase ("transcriptase") as a signal to bind to the nucleic acid and begin the transcription of RNA at a specific site.

As used herein, a "promoter provider" or "provider" refers to an oligonucleotide comprising first and second regions, and which is modified to prevent the initiation of DNA synthesis from its 3'-terminus. The "first region" of a promoter provider oligonucleotide comprises a base sequence which hybridizes to a DNA template, where the hybridizing sequence is situated 3', but not necessarily adjacent to, a promoter region. The hybridizing portion of a promoter oligonucleotide is typically at least 10 nucleotides in length, and may extend up to 50 or more nucleotides in length. The "second region" comprises a promoter sequence for an RNA polymerase. A promoter oligonucleotide is engineered so that it is incapable of being extended by an RNA- or DNA-dependent DNA polymerase, e.g., reverse transcriptase, preferably comprising a blocking moiety at its 3'-terminus as described above. As referred to herein, a "T7 Provider" is a blocked promoter provider oligonucleotide that provides an oligonucleotide sequence that is recognized by T7 RNA polymerase.

A "terminating oligonucleotide" is an oligonucleotide comprising a base sequence that is substantially complementary to a sequence within the target nucleic acid in the vicinity of the 5'-end of the target region, so as to "terminate" primer extension of a nascent nucleic acid that includes a priming oligonucleotide, thereby providing a defined 3'-end for the nascent nucleic acid strand. A terminating oligonucleotide is designed to hybridize to the target nucleic acid at a position sufficient to achieve the desired 3'-end for the nascent nucleic acid strand. The positioning of the terminating oligonucleotide is flexible depending upon its design. A terminating oligonucleotide may be modified or unmodified. In certain embodiments, terminating oligonucleotides are synthesized with at least one or more 2'-O-ME ribonucleotides. These modified nucleotides have demonstrated higher thermal stability of complementary duplexes. The 2'-O-ME ribonucleotides also function to increase the resistance of oligonucleotides to exonucleases, thereby increasing the half-life of the modified oligonucleotides. (See, e.g., Majlessi et al., *Nucleic Acids Res.* 26:2224-9, 1988, incorporated by reference herein.) Other modifications as described elsewhere herein may be utilized in addition to or in place of 2'-O-ME ribonucleotides. For example, a terminating oligonucleotide may comprise PNA or an LNA. (See, e.g., Petersen et al., *J. Mol. Recognit.* 13:44-53, 2000, incorporated by reference herein.) A terminating oligonucleotide of the present invention typically includes a blocking moiety at its 3'-terminus to prevent extension. A terminating oligonucleotide may also comprise a protein or peptide joined to the oligonucleotide so as to terminate further extension of a nascent nucleic acid chain by a polymerase. A terminating oligonucleotide of the present invention is typically at least 10 bases in length, and may extend up to 15, 20, 25, 30, 35, 40, 50 or more nucleotides in length. While a terminating oligonucleotide typically or necessarily includes a 3'-blocking moiety, "3'-blocked" oligonucleotides are not necessarily terminating oligonucleotides.

An "extender oligomer" or "extend oligomer" as used herein refers to an oligonucleotide that is the same sense as the T7 Provider and may act as a helper oligonucleotide that opens up structure or improves specificity.

"Amplification" refers to any known procedure for obtaining multiple copies of a target nucleic acid sequence or its complement or fragments thereof. The multiple copies may be referred to as amplicons or amplification products. Amplification of "fragments" refers to production of an amplified nucleic acid that contains less than the complete target nucleic acid or its complement, e.g., produced by using an amplification oligonucleotide that hybridizes to, and initiates polymerization from, an internal position of the target nucleic acid. Known amplification methods include, for example, replicase-mediated amplification, polymerase chain reaction (PCR), ligase chain reaction (LCR), strand-displacement amplification (SDA), and transcription-mediated or transcription-associated amplification. Replicase-mediated amplification uses self-replicating RNA molecules, and a replicase such as QB-replicase (see, e.g., U.S. Pat. No. 4,786,600, incorporated by reference herein). PCR amplification uses a DNA polymerase, pairs of primers, and thermal cycling to synthesize multiple copies of two complementary strands of dsDNA or from a cDNA (see, e.g., U.S. Pat. Nos. 4,683,195; 4,683,202; and 4,800,159; each incorporated by reference herein). LCR amplification uses four or more different oligonucleotides to amplify a target and its complementary strand by using multiple cycles of hybridization, ligation, and denaturation (see, e.g., U.S. Pat. Nos. 5,427,930 and 5,516,663, each incorporated by reference herein). SDA uses a primer that contains a recognition site for a restriction endonuclease and an endonuclease that nicks one strand of a hemimodified DNA duplex that includes the target sequence, whereby amplification occurs in a series of primer extension and strand displacement steps (see, e.g., U.S. Pat. Nos. 5,422,252; 5,547,861; and 5,648,211; each incorporated by reference herein).

"Transcription-associated amplification" or "transcription-mediated amplification" (TMA) refer to nucleic acid amplification that uses an RNA polymerase to produce multiple RNA transcripts from a nucleic acid template. These methods generally employ an RNA polymerase, a DNA polymerase, deoxyribonucleoside triphosphates, ribonucleoside triphosphates, and a template complementary oligonucleotide that includes a promoter sequence, and optionally may include one or more other oligonucleotides. TMA methods and single-primer transcription associated amplification method are embodiments of amplification methods used for detection of *G. vaginalis* target sequences as described herein. Variations of transcription-associated amplification are well known in the art as previously disclosed in detail (see, e.g., U.S. Pat. Nos. 4,868,105; 5,124,246; 5,130,238; 5,399,491; 5,437,990; 5,554,516; and 7,374,885; and International Patent Application Pub. Nos. WO 88/01302; WO 88/10315; and WO 95/03430; each incorporated by reference herein). The person of ordinary skill in the art will appreciate that the disclosed compositions may be used in amplification methods based on extension of oligomer sequences by a polymerase.

As used herein, the term "real-time TMA" refers to single-primer transcription-mediated amplification ("TMA") of target nucleic acid that is monitored by real-time detection means.

The term "amplicon" or the term "amplification product" as used herein refers to the nucleic acid molecule generated during an amplification procedure that is complementary or homologous to a sequence contained within the target sequence. The complementary or homologous sequence of an amplicon is sometimes referred to herein as a "target-specific sequence." Amplicons generated using the amplification oligomers of the current invention may comprise non-target specific sequences. Amplicons can be double stranded or single stranded and can include DNA, RNA or both. For example, DNA-dependent RNA polymerase transcribes single stranded amplicons from double-stranded DNA during transcription-mediated amplification procedures. These single-stranded amplicons are RNA amplicons and can be either strand of a double-stranded complex, depending on how the amplification oligomers are configured. Thus, amplicons can be single-stranded RNA. RNA-dependent DNA polymerases synthesize a DNA strand that is complementary to an RNA template. Thus, amplicons can be double-stranded DNA and RNA hybrids. RNA-dependent DNA polymerases often include RNase activity, or are used in conjunction with an RNase, which degrades the RNA strand. Thus, amplicons can be single stranded DNA. RNA-dependent DNA polymerases and DNA-dependent DNA polymerases synthesize complementary DNA strands from DNA templates. Thus, amplicons can be double-stranded DNA. RNA-dependent RNA polymerases synthesize RNA from an RNA template. Thus, amplicons can be double-stranded RNA. DNA-dependent RNA polymerases synthesize RNA from double-stranded DNA templates, also referred to as transcription. Thus, amplicons can be single stranded RNA. Amplicons and methods for generating amplicons are known to those skilled in the art. For convenience herein, a single strand of RNA or a single strand of DNA may represent an amplicon generated by an amplification oligomer combination of the current invention. Such representation is not meant to limit the amplicon to the representation shown. Skilled artisans in possession of the instant disclosure will use amplification oligomers and polymerase enzymes to generate any of the numerous types of amplicons, all within the spirit and scope of the current invention.

A "non-target-specific sequence," as is used herein refers to a region of an oligomer sequence, wherein said region does not stably hybridize with a target sequence under standard hybridization conditions. Oligomers with non-target-specific sequences include, but are not limited to, promoter primers and molecular beacons. An amplification oligomer may contain a sequence that is not complementary to the target or template sequence; for example, the 5' region of a primer may include a promoter sequence that is non-complementary to the target nucleic acid (referred to as a "promoter primer"). Those skilled in the art will understand that an amplification oligomer that functions as a primer may be modified to include a 5' promoter sequence, and thus function as a promoter primer. Similarly, a promoter primer may be modified by removal of, or synthesis without, a promoter sequence and still function as a primer. A 3' blocked amplification oligomer may provide a promoter sequence and serve as a template for polymerization (referred to as a "promoter provider"). Thus, an amplicon that is generated by an amplification oligomer member such as a promoter primer will comprise a target-specific sequence and a non-target-specific sequence.

"Detection probe," "detection oligonucleotide," and "detection probe oligomer" are used interchangeably to refer to a nucleic acid oligomer that hybridizes specifically to a target sequence in a nucleic acid, or in an amplified nucleic acid, under conditions that promote hybridization to allow detection of the target sequence or amplified nucleic acid. Detection may either be direct (e.g., a probe hybridized directly to its target sequence) or indirect (e.g., a probe linked to its target via an intermediate molecular structure). Detection probes may be DNA, RNA, analogs thereof or combinations thereof and they may be labeled or unlabeled. Detection probes may further include alternative backbone linkages such as, e.g., 2'-O-methyl linkages. A detection probe's "target sequence" generally refers to a smaller nucleic acid sequence region within a larger nucleic acid sequence that hybridizes specifically to at least a portion of a probe oligomer by standard base pairing. A detection probe may comprise target-specific sequences and other sequences that contribute to the three-dimensional conformation of the probe (see, e.g., U.S. Pat. Nos. 5,118,801; 5,312,728; 6,849,412; 6,835,542; 6,534,274; and 6,361,945; and US Patent Application Pub. No. 20060068417; each incorporated by reference herein).

By "stable" or "stable for detection" is meant that the temperature of a reaction mixture is at least 2° C. below the melting temperature of a nucleic acid duplex.

As used herein, a "label" refers to a moiety or compound joined directly or indirectly to a probe that is detected or leads to a detectable signal. Direct labeling can occur through bonds or interactions that link the label to the probe, including covalent bonds or non-covalent interactions, e.g., hydrogen bonds, hydrophobic and ionic interactions, or formation of chelates or coordination complexes. Indirect labeling can occur through use of a bridging moiety or "linker" such as a binding pair member, an antibody or additional oligomer, which is either directly or indirectly labeled, and which may amplify the detectable signal. Labels include any detectable moiety, such as a radionuclide, ligand (e.g., biotin, avidin), enzyme or enzyme substrate, reactive group, or chromophore (e.g., dye, particle, or bead that imparts detectable color), luminescent compound (e.g., bioluminescent, phosphorescent, or chemiluminescent labels), or fluorophore. Labels may be detectable in a homogeneous assay in which bound labeled probe in a mixture exhibits a detectable change different from that of an unbound labeled probe, e.g., instability or differential degradation properties. A "homogeneous detectable label" can be detected without physically removing bound from unbound forms of the label or labeled probe (see, e.g., U.S. Pat. Nos. 5,283,174; 5,656,207; and 5,658,737; each incorporated by reference herein). Labels include chemiluminescent compounds, e.g., acridinium ester ("AE") compounds that include standard AE and derivatives (see, e.g., U.S. Pat. Nos. 5,656,207; 5,658,737; and 5,639,604; each incorporated by reference herein). Synthesis and methods of attaching labels to nucleic acids and detecting labels are well known. (See, e.g., Sambrook et al., *Molecular Cloning, A Laboratory Manual,* 2nd ed. (Cold Spring Harbor Laboratory Press, Cold Spring Harbor, N.Y., 1989), Chapter 10, incorporated by reference herein. See also U.S. Pat. Nos. 5,658,737; 5,656,207; 5,547,842; 5,283,174; and 4,581,333; each incorporated by reference herein). More than one label, and more than one type of label, may be present on a particular probe, or detection may use a mixture of probes in which each probe is labeled with a compound that produces a detectable signal (see, e.g., U.S. Pat. Nos. 6,180,340 and 6,350,579, each incorporated by reference herein).

"Capture probe," "capture oligonucleotide," and "capture probe oligomer" are used interchangeably to refer to a nucleic acid oligomer that specifically hybridizes to a target sequence in a target nucleic acid by standard base pairing and joins to a binding partner on an immobilized probe to capture the target nucleic acid to a support. One example of a capture oligomer includes two binding regions: a sequence-binding region (e.g., target-specific portion) and an immobilized probe-binding region, usually on the same oligomer, although the two regions may be present on two different oligomers joined together by one or more linkers. Another embodiment of a capture oligomer uses a target-sequence binding region that includes random or non-random poly-GU, poly-GT, or poly U sequences to bind non-specifically to a target nucleic acid and link it to an immobilized probe on a support.

As used herein, an "immobilized oligonucleotide," "immobilized probe," or "immobilized nucleic acid" refers to a nucleic acid binding partner that joins a capture oligomer to a support, directly or indirectly. An immobilized probe joined to a support facilitates separation of a capture probe bound target from unbound material in a sample. One embodiment of an immobilized probe is an oligomer joined to a support that facilitates separation of bound target sequence from unbound material in a sample. Supports may include known materials, such as matrices and particles free in solution, which may be made of nitrocellulose, nylon, glass, polyacrylate, mixed polymers, polystyrene, silane, polypropylene, metal, or other compositions, of which one embodiment is magnetically attractable particles. Supports may be monodisperse magnetic spheres (e.g., uniform size±5%), to which an immobilized probe is joined directly (via covalent linkage, chelation, or ionic interaction), or indirectly (via one or more linkers), where the linkage or interaction between the probe and support is stable during hybridization conditions.

By "complementary" is meant that the nucleotide sequences of similar regions of two single-stranded nucleic acids, or to different regions of the same single-stranded nucleic acid have a nucleotide base composition that allow the single-stranded regions to hybridize together in a stable double-stranded hydrogen-bonded region under stringent hybridization or amplification conditions. Sequences that hybridize to each other may be completely complementary or partially complementary to the intended target sequence by standard nucleic acid base pairing (e.g., G:C, A:T or A:U pairing). By "sufficiently complementary" is meant a contiguous sequence that is capable of hybridizing to another sequence by hydrogen bonding between a series of complementary bases, which may be complementary at each position in the sequence by standard base pairing or may contain one or more residues, including abasic residues, that are not complementary. Sufficiently complementary contiguous sequences typically are at least 80%, or at least 90%, complementary to a sequence to which an oligomer is intended to specifically hybridize. Sequences that are "sufficiently complementary" allow stable hybridization of a nucleic acid oligomer with its target sequence under appropriate hybridization conditions, even if the sequences are not completely complementary. When a contiguous sequence of nucleotides of one single-stranded region is able to form a series of "canonical" hydrogen-bonded base pairs with an analogous sequence of nucleotides of the other single-stranded region, such that A is paired with U or T and C is paired with G, the nucleotides sequences are "completely" complementary (see, e.g., Sambrook et al., *Molecular Cloning, A Laboratory Manual,* $2^{nd}$ ed. (Cold Spring Harbor Laboratory Press, Cold Spring Harbor, N.Y., 1989) at §§1.90-1.91, 7.37-7.57, 9.47-9.51 and 11.47-11.57, particularly §§9.50-9.51, 11.12-11.13, 11.45-11.47 and 11.55-11.57, incorporated by reference herein). It is understood that ranges for percent identity are inclusive of all whole and partial numbers (e.g., at least 90% includes 90, 91, 93.5, 97.687 and etc.).

By "preferentially hybridize" or "specifically hybridize" is meant that under stringent hybridization assay conditions, probes hybridize to their target sequences, or replicates thereof, to form stable probe:target hybrids, while at the same time formation of stable probe:non-target hybrids is minimized Thus, a probe hybridizes to a target sequence or replicate thereof to a sufficiently greater extent than to a non-target sequence, to enable one having ordinary skill in the art to accurately quantitate the RNA replicates or complementary DNA (cDNA) of the target sequence formed during the amplification. Appropriate hybridization conditions are well-known in the art, may be predicted based on sequence composition, or can be determined by using routine testing methods (see, e.g., Sambrook et al., *Molecular Cloning, A Laboratory Manual,* $2^{nd}$ ed. (Cold Spring Harbor Laboratory Press, Cold Spring Harbor, N.Y., 1989) at §§1.90-1.91, 7.37-7.57, 9.47-9.51 and 11.47-11.57, particularly §§9.50-9.51, 11.12-11.13, 11.45-11.47 and 11.55-11.57, incorporated by reference herein).

By "nucleic acid hybrid," "hybrid," or "duplex" is meant a nucleic acid structure containing a double-stranded, hydrogen-bonded region wherein each strand is complementary to the other, and wherein the region is sufficiently stable under stringent hybridization conditions to be detected by means including, but not limited to, chemiluminescent or fluorescent light detection, autoradiography, or gel electrophoresis. Such hybrids may comprise RNA:RNA, RNA:DNA, or DNA:DNA duplex molecules.

"Sample preparation" refers to any steps or method that treats a sample for subsequent amplification and/or detection of *Gardnerella vaginalis* nucleic acids present in the sample. Samples may be complex mixtures of components of which the target nucleic acid is a minority component. Sample preparation may include any known method of concentrating components, such as microbes or nucleic acids, from a larger sample volume, such as by filtration of airborne or waterborne particles from a larger volume sample or by isolation of microbes from a sample by using standard microbiology methods. Sample preparation may include physical disruption and/or chemical lysis of cellular components to release intracellular components into a substantially aqueous or organic phase and removal of debris, such as by using filtration, centrifugation or adsorption. Sample preparation may include use of a nucleic acid oligonucleotide that selectively or non-specifically capture a target nucleic acid and separate it from other sample components (e.g., as described in U.S. Pat. No. 6,110,678 and International Patent Application Pub. No. WO 2008/016988, each incorporated by reference herein).

"Separating" or "purifying" means that one or more components of a sample are removed or separated from other sample components. Sample components include target nucleic acids usually in a generally aqueous solution phase, which may also include cellular fragments, proteins, carbohydrates, lipids, and other nucleic acids. Separating or purifying removes at least 70%, or at least 80%, or at least 95% of the target nucleic acid from other sample components.

As used herein, a "DNA-dependent DNA polymerase" is an enzyme that synthesizes a complementary DNA copy from a DNA template. Examples are DNA polymerase I from E. coli, bacteriophage T7 DNA polymerase, or DNA polymerases from bacteriophages T4, Phi-29, M2, or T5. DNA-dependent DNA polymerases may be the naturally occurring enzymes isolated from bacteria or bacteriophages or expressed recombinantly, or may be modified or "evolved" forms which have been engineered to possess certain desirable characteristics, e.g., thermostability, or the ability to recognize or synthesize a DNA strand from various modified templates. All known DNA-dependent DNA polymerases require a complementary primer to initiate synthesis. It is known that under suitable conditions a DNA-dependent DNA polymerase may synthesize a complementary DNA copy from an RNA template. RNA-dependent DNA polymerases typically also have DNA-dependent DNA polymerase activity.

As used herein, a "DNA-dependent RNA polymerase" or "transcriptase" is an enzyme that synthesizes multiple RNA copies from a double-stranded or partially double-stranded DNA molecule having a promoter sequence that is usually double-stranded. The RNA molecules ("transcripts") are synthesized in the 5'-to-3' direction beginning at a specific position just downstream of the promoter. Examples of transcriptases are the DNA-dependent RNA polymerase from E. coli and bacteriophages T7, T3, and SP6.

As used herein, an "RNA-dependent DNA polymerase" or "reverse transcriptase" ("RT") is an enzyme that synthesizes a complementary DNA copy from an RNA template. All known reverse transcriptases also have the ability to make a complementary DNA copy from a DNA template; thus, they are both RNA- and DNA-dependent DNA polymerases. RTs may also have an RNAse H activity. A primer is required to initiate synthesis with both RNA and DNA templates.

As used herein, a "selective RNAse" is an enzyme that degrades the RNA portion of an RNA:DNA duplex but not single-stranded RNA, double-stranded RNA or DNA. An exemplary selective RNAse is RNAse H. Enzymes possessing the same or similar activity as RNAse H may also be used. Selective RNAses may be endonucleases or exonucleases. Most reverse transcriptase enzymes contain an RNAse H activity in addition to their polymerase activities. However, other sources of the RNAse H are available without an associated polymerase activity. The degradation may result in separation of RNA from a RNA:DNA complex. Alternatively, a selective RNAse may simply cut the RNA at various locations such that portions of the RNA melt off or permit enzymes to unwind portions of the RNA. Other enzymes that selectively degrade RNA target sequences or RNA products of the present invention will be readily apparent to those of ordinary skill in the art.

The term "specificity," in the context of an amplification and/or detection system, is used herein to refer to the characteristic of the system which describes its ability to distinguish between target and non-target sequences dependent on sequence and assay conditions. In terms of nucleic acid amplification, specificity generally refers to the ratio of the number of specific amplicons produced to the number of side-products (e.g., the signal-to-noise ratio). In terms of detection, specificity generally refers to the ratio of signal produced from target nucleic acids to signal produced from non-target nucleic acids.

The term "sensitivity" is used herein to refer to the precision with which a nucleic acid amplification reaction can be detected or quantitated. The sensitivity of an amplification reaction is generally a measure of the smallest copy number of the target nucleic acid that can be reliably detected in the amplification system, and will depend, for example, on the detection assay being employed, and the specificity of the amplification reaction, e.g., the ratio of specific amplicons to side-products.

As used herein, a "colony-forming unit" ("CFU") is used as a measure of viable microorganisms in a sample. A CFU is an individual viable cell capable of forming on a solid medium a visible colony whose individual cells are derived by cell division from one parental cell. One CFU corresponds to ~1000 copies of rRNA.

As used herein, the term "relative light unit" ("RLU") is an arbitrary unit of measurement indicating the relative number of photons emitted by the sample at a given wavelength or band of wavelengths. RLU varies with the characteristics of the detection means used for the measurement.

BRIEF DESCRIPTION OF THE DRAWINGS

FIG. 1 illustrates a reference sequence for Gardnerella vaginalis 16S ribosomal rRNA gene (SEQ ID NO:88), partial sequence found at GenBank under accession number EF194095.1 and GI:122938535.

DETAILED DESCRIPTION OF THE INVENTION

The present invention provides compositions, kits and methods for amplifying and detecting Gardnerella vaginalis (G. vaginalis or "GV") nucleic acid from a sample, specifically sequences of GV 16S rRNA or genes encoding 16S rRNA. Preferably, the samples are biological samples. The compositions, kits and methods provide oligonucleotide sequences that recognize target sequences of GV 16S rRNA or their complementary sequences, or genes encoding 16S rRNA or their complementary sequences. Such oligonucleotides may be used as amplification oligonucleotides, which may include primers, promoter primers, blocked oligonucleotides, and promoter provider oligonucleotides, whose functions have been described previously (see, e.g., U.S. Pat. Nos. 4,683,195; 4,683,202; 4,800,159; 5,399,491; 5,554,516; 5,824,518; and 7,374,885; each incorporated by reference herein). Other oligonucleotides may be used as probes for detecting amplified sequences of G. vaginalis.

The methods provide for the sensitive and specific detection of G. vaginalis nucleic acids. The methods include performing a nucleic acid amplification of GV sequences and detecting the amplified product by, for example, specifically hybridizing the amplified product with a nucleic acid detection probe that provides a signal to indicate the presence of GV in the sample. The amplification step includes contacting the sample with one or more amplification oligomers specific for a target sequence in 16S rRNA to produce an amplified product if *G. vaginalis* nucleic acid is present in the sample. Amplification synthesizes additional copies of the target sequence or its complement by using at least one nucleic acid polymerase to extend the sequence from an amplification oligomer (a primer) using a template strand. One embodiment for detecting the amplified product uses a hybridizing step that includes contacting the amplified product with at least one probe specific for a sequence amplified by the selected amplification oligomers, e.g., a sequence contained in the target sequence flanked by a pair of selected primers.

The detection step may be performed using any of a variety of known techniques to detect a signal specifically associated with the amplified target sequence, such as, e.g., by hybridizing the amplification product with a labeled detection probe and detecting a signal resulting from the labeled probe. The detection step may also provide additional information on the amplified sequence, such as, e.g., all or a portion of its nucleic acid base sequence. Detection may be performed after the amplification reaction is completed, or may be performed simultaneously with amplifying the target region, e.g., in real time. In one embodiment, the detection step allows homogeneous detection, e.g., detection of the hybridized probe without removal of unhybridized probe from the mixture (see, e.g., U.S. Pat. Nos. 5,639,604 and 5,283,174, each incorporated by reference herein).

In embodiments that detect the amplified product near or at the end of the amplification step, a linear detection probe may be used to provide a signal to indicate hybridization of the probe to the amplified product. One example of such detection uses a luminescently labeled probe that hybridizes to target nucleic acid. Luminescent label is then hydrolyzed from non-hybridized probe. Detection is performed by chemiluminescence using a luminometer. (see, e.g., International Patent Application Pub. No. WO 89/002476, incorporated by reference herein). In other embodiments that use real-time detection, the detection probe may be a hairpin probe such as, for example, a molecular beacon, molecular torch, or hybridization switch probe that is labeled with a reporter moiety that is detected when the probe binds to amplified product. Such probes may comprise target-hybridizing sequences and non-target-hybridizing sequences. Various forms of such probes have been described previously (see, e.g., U.S. Pat. Nos. 5,118,801; 5,312,728; 5,925,517; 6,150,097; 6,849,412; 6,835,542; 6,534,274; and 6,361,945; and US Patent Application Pub. Nos. 20060068417A1 and 20060194240A1; each incorporated by reference herein).

Preferred compositions of the instant invention are configured to specifically hybridize to a 16S rRNA nucleic acid of *G. vaginalis* with minimal cross-reactivity to other nucleic acids suspected of being in a sample. In some aspects, the compositions of the instant invention are configured to specifically hybridize to a 16S rRNA nucleic acid of *G. vaginalis* with minimal cross-reactivity to one or more of anaerobic gram-positive cocci; *A. vaginae; Lactobacillus* sp.; *Lactobacillus iners; Lactobacillus crispatus* group; *Lactobacillus gasseri* group; *Trichomonas* sp.; *Trichomonas vaginalis; Candida* sp.; *Eggerthella* sp.; Bacterium from the order Clostridiales; *Clostridium*-like sp.; *Prevotella* sp.; *Prevotella bivia* group; *Prevotella buccalis* group; *Atopobium* sp.; *Atopobium vaginae; Enterobacteria; Peptostreptococcus micros; Aerococcus christensenii; Leptotrichia amnionii; Peptoniphilus* sp.; *Dialister* sp.; *Mycoplasma hominis; Sneathia sanguinegens; Anaerococcus tetradius; Mobiluncus* sp.; *Mobiluncus hominis; Eggerthella hongkongensis; Megasphaera* sp.; *Leptotrichia sanguinegens* and *Finegoldia magna*. In one aspect, the compositions of the instant invention are part of a multiplex system that further includes components and methods for detecting one of more of these organisms.

In certain aspects of the invention, a combination of at least two oligomers is provided for the detection of a *G. vaginalis* 16S rRNA or a gene encoding a *G. vaginalis* 16S rRNA. Typically, the oligomer combination includes first and second amplification oligomers for amplifying a GV nucleic acid target region corresponding to SEQ ID NO:88 from about nucleotide position 164 to about nucleotide position 205. For example, in some embodiments, the first amplification oligomer comprises a first target-hybridizing sequence that is from about 15 to about 27 contiguous nucleotides in length and substantially corresponding to, or identical to, a sequence that is contained in the sequence of SEQ ID NO:75 and that includes SEQ ID NO:72 and/or SEQ ID NO:73; and the second amplification oligomer comprises a second target-hybridizing sequence that is from about 15 to about 27 contiguous nucleotides in length and substantially corresponding to, or identical to, a sequence that is contained in the sequence of SEQ ID NO:71 and that includes at least the sequence of SEQ ID NO:70.

In some embodiments of the oligomer combination, the first target-hybridizing sequence is selected from the following: (a) a sequence substantially corresponding to, or identical to, a sequence that is contained in the sequence of SEQ ID NO:76; (b) a sequence substantially corresponding to, or identical to, a sequence that is contained in the sequence of SEQ ID NO:78; (c) a sequence substantially corresponding to, or identical to, a sequence that is contained in the sequence of SEQ ID NO:79; and (d) a sequence substantially corresponding to, or identical to, a sequence that is contained in the sequence of SEQ ID NO:81. In more particular variations, a first target-hybridizing sequence as in (a)-(d) above is as follows: for the target-hybridizing sequence of (a), a sequence substantially corresponding to, or identical to, a sequence that includes at least the sequence of SEQ ID NO:72; for the target-hybridizing sequence of (b), a sequence substantially corresponding to, or identical to, a sequence that includes at least the sequence of SEQ ID NO:77; for the target-hybridizing sequence of (c), a sequence substantially corresponding to, or identical to, a sequence that includes at least the sequence of SEQ ID NO:73; and for the target-hybridizing sequence of (d), a sequence substantially corresponding to, or identical to, a sequence that includes at least the sequence of SEQ ID NO:80. In specific variations, the first target-hybridizing sequence of (a) substantially corresponds to, or is identical to, the sequence shown in SEQ ID NO:6, SEQ ID NO:7, or SEQ ID NO:8; the first target-hybridizing sequence of (b) substantially corresponds to, or is identical to, the sequence shown in SEQ ID NO:7 or SEQ ID NO:8; the first target-hybridizing sequence of (c) substantially corresponds to, or is identical to, the sequence shown in SEQ ID NO:7, SEQ ID NO:8, SEQ ID NO:9, or SEQ ID NO:10; or the first target-hybridizing sequence of (d) substantially corresponds to, or is identical to, the sequence shown in SEQ ID NO:9 or SEQ ID NO:10.

In certain embodiments, the second target-hybridizing sequence is selected from the following: (a) a sequence substantially corresponding to, or identical to, the sequence shown in SEQ ID NO:35, SEQ ID NO:36, SEQ ID NO:37, SEQ ID NO:38, or SEQ ID NO:39; and (b) a sequence substantially corresponding to, or identical to, a sequence that is contained in the sequence of SEQ ID NO:86. In some embodiments of a second target-hybridizing sequence as in (b) above, the target-hybridizing sequence substantially corresponds to, or is identical to, a sequence that includes at least the sequence of SEQ ID NO:85. In specific variations, a second target-hybridizing sequence as in (b) substantially corresponds to, or is identical to, the sequence shown in SEQ ID NO:36, SEQ ID NO:38, or SEQ ID NO:39.

In certain embodiments, an amplification oligomer as described herein is a promoter primer or promoter provider further comprising a promoter sequence located 5' to the target-hybridizing sequence and which is non-complementary to the *G. vaginalis* target nucleic acid. For example, in some embodiments of an oligomer combination as described herein for amplification of a GV target region, the second amplification oligomer is a promoter primer or promoter provider further comprising a 5' promoter sequence. In particular embodiments, the promoter sequence is a T7 RNA polymerase promoter sequence such as, for example, a T7 promoter sequence having the sequence shown in SEQ ID NO:87. In specific variations, the second amplification oligomer is a promoter primer or promoter provider having the sequence shown in SEQ ID NO:1, SEQ ID NO:2, SEQ ID NO:3, SEQ ID NO:4, or SEQ ID NO:5.

In some embodiments, an oligomer combination as described herein further includes a terminating oligonucleotide (also referred to herein as a "blocker" oligonucleotide) comprising comprises a base sequence substantially complementary (e.g., fully complementary) to a sequence contained within the target nucleic acid in the vicinity of the 5'-end of the target region. A terminating oligomer is typically used in combination with, e.g., a promoter provider amplification oligomer, such as, for example, in certain embodiments described herein relating to transcription-mediated amplification (TMA). Particular suitable terminating oligomers for use in accordance with the present invention have a sequence substantially corresponding to, or identical to, a sequence selected from SEQ ID NO:11, SEQ ID NO:12, SEQ ID NO:13, SEQ ID NO:14, SEQ ID NO:15, and SEQ ID NO:16.

In some embodiments, an oligomer combination as described herein further comprises at least one capture probe oligomer comprising a target-hybridizing sequence substantially corresponding to a sequence contained in the complement of SEQ ID NO:88, wherein the target-hybridizing sequence is covalently attached to a sequence or moiety that binds to an immobilized probe. In specific variations, the target-hybridizing sequence comprises or consists of a sequence substantially corresponding to, or identical to, a sequence selected from SEQ ID NO:40, SEQ ID NO:41, SEQ ID NO:42, SEQ ID NO:43, SEQ ID NO:44, SEQ ID NO:45, and SEQ ID NO:46. Particularly suitable capture probes for use in accordance with the present invention comprise or consist of a sequence selected from SEQ ID NO:25, SEQ ID NO:26, SEQ ID NO:27, SEQ ID NO:28, SEQ ID NO:29, SEQ ID NO:30, and SEQ ID NO:31.

In certain variations, an oligomer combination as described herein further comprises at least one detection probe oligomer configured to specifically hybridize to a *G. vaginalis* target sequence that is amplifiable using the first and second amplification oligomers (e.g., a GV target sequence that is flanked by the target-hybridizing sequences of the first and second amplification oligomers). In some embodiments, a detection probe oligomer for use in accordance with the present invention comprises a target-hybridizing sequence that is from about 14 to about 35 nucleotides in length and is configured to specifically hybridize to a target sequence contained within SEQ ID NO:88 from about nucleotide position 164 to about nucleotide position 205.

For example, in some variations, the detection probe target-hybridizing sequence is contained in the sequence of SEQ ID NO:84 and/or includes at least the sequence of SEQ ID NO:83. Particularly suitable detection probe oligomers include, for example, oligomers comprising a target-hybridizing sequence substantially corresponding to, or identical to, a sequence selected from SEQ ID NO:20, SEQ ID NO:21, SEQ ID NO:22, SEQ ID NO:23, and SEQ ID NO:24.

Typically, a detection probe oligomer in accordance with the present invention further includes a label. Particularly suitable labels include compounds that emit a detectable light signal, e.g., fluorophores or luminescent (e.g., chemiluminescent) compounds that can be detected in a homogeneous mixture. More than one label, and more than one type of label, may be present on a particular probe, or detection may rely on using a mixture of probes in which each probe is labeled with a compound that produces a detectable signal (see, e.g., U.S. Pat. Nos. 6,180,340 and 6,350,579, each incorporated by reference herein). Labels may be attached to a probe by various means including covalent linkages, chelation, and ionic interactions, but preferably the label is covalently attached. For example, in some embodiments, a detection probe has an attached chemiluminescent label such as, e.g., an acridinium ester (AE) compound (see, e.g., U.S. Pat. Nos. 5,185,439; 5,639,604; 5,585,481; and 5,656,744; each incorporated by reference herein), which in typical variations is attached to the probe by a non-nucleotide linker (see, e.g., U.S. Pat. Nos. 5,585,481; 5,656,744; and 5,639,604, particularly at column 10, line 6 to column 11, line 3, and Example 8; each incorporated by reference herein). In other embodiments, a detection probe comprises both a fluorescent label and a quencher, a combination that is particularly useful in fluorescence resonance energy transfer (FRET) assays. Specific variations of such detection probes include, e.g., a TaqMan detection probe (Roche Molecular Diagnostics) and a "molecular beacon" (see, e.g., Tyagi et al., *Nature Biotechnol.* 16:49-53, 1998; U.S. Pat. Nos. 5,118,801 and 5,312,728; each incorporated by reference herein).

A detection probe oligomer in accordance with the present invention may further include a non-target-hybridizing sequence. Specific embodiments of such detection probes include, for example, probes that form conformations held by intramolecular hybridization, such as conformations generally referred to as hairpins. Particularly suitable hairpin probes include a "molecular torch" (see, e.g., U.S. Pat. Nos. 6,849,412; 6,835,542; 6,534,274; and 6,361,945, each incorporated by reference herein) and a "molecular beacon" (see, e.g., Tyagi et al., supra; U.S. Pat. No. 5,118,801 and U.S. Pat. No. 5,312,728, supra). Methods for using such hairpin probes are well known in the art.

In yet other embodiments, a detection probe is a linear oligomers that does not substantially form conformations held by intramolecular bonds. In specific variations, a linear detection probe oligomer includes a chemiluminescent compound as the label, preferably an acridinium ester (AE) compound.

In yet other variations, an oligomer combination for detection of a *G. vaginalis* nucleic acid further comprises a pseudotarget oligomer that can be amplified using first and second amplification oligomers as described herein. Typically, the pseudotarget oligomer is sufficiently distinct from the target region of GV nucleic acid flanked by the amplification oligomers, such that a detection probe configured to specifically hybridize to a GV-specific amplification product, generated using the amplification oligomers on a GV target nucleic acid template, will not specifically hybridize to an amplification product generated using the same amplification oligomers with the pseudotarget oligomer template. Pseudotargets may be used to adjust assay sensitivity by changing the cutoff used to classify a sample as positive or negative, rather than re-optimizing the entire amp system to get lower sensitivity through lower amplification efficiency. Accordingly, such pseudotarget oligomers are particularly useful for "detuning" assay sensitivity in certain embodiments of the detection methods described herein. In a specific embodiment, the pseudotarget oligomer has a sequence substantially corresponding to, or identical to, SEQ ID NO:34 (amplifiable using, e.g., amplification oligomers comprising target-hybridizing sequences of SEQ ID NO:8 and SEQ ID NO:39).

Also provided by the present invention are detection probe oligomers, capture probe oligomers, and pseudotarget oligomers as described herein.

In another aspect, the present invention provides methods for detecting a G. vaginalis 16S rRNA or a gene encoding a G. vaginalis 16S rRNA in a sample using an oligomer combination as described herein. Such a method generally includes (a) contacting the sample with at least two oligomers for amplifying a GV nucleic acid target region corresponding to a GV 16S rRNA target nucleic acid, where the oligomer combination includes first and second amplification oligomers as described above; (b) performing an in vitro nucleic acid amplification reaction, where any GV target nucleic acid present in the sample is used as a template for generating an amplification product; and (c) detecting the presence or absence of the amplification product, thereby indicating the presence or absence of GV in the sample. A detection method in accordance with the present invention typically further includes the step of obtaining the sample to be contacted with the at least two oligomers. In certain embodiments, "obtaining" a sample to be used in steps (a)-(c) includes, for example, receiving the sample at a testing facility or other location where one or more steps of the method are performed, and/or retrieving the sample from a location (e.g., from storage or other depository) within a facility where one or more steps of the method are performed.

In certain embodiments, the method further includes purifying the *Gardnerella vaginalis* target nucleic acid from other components in the sample before the contacting step. Such purification may include may include methods of separating and/or concentrating organisms contained in a sample from other sample components. In particular embodiments, purifying the target nucleic acid includes capturing the target nucleic acid to specifically or non-specifically separate the target nucleic acid from other sample components. Non-specific target capture methods may involve selective precipitation of nucleic acids from a substantially aqueous mixture, adherence of nucleic acids to a support that is washed to remove other sample components, or other means of physically separating nucleic acids from a mixture that contains G. vaginalis nucleic acid and other sample components.

In some embodiments, a 16S rRNA target nucleic of G. vaginalis or a gene encoding the 16S rRNA of G. vaginalis is selectively separated from other sample components by specifically hybridizing the GV target nucleic acid to a capture probe oligomer. The capture probe oligomer comprises a target-hybridizing sequence configured to specifically hybridize to a GV 16S rRNA target sequence so as to form a target-sequence:capture-probe complex that is separated from sample components. Suitable capture probe target-hybridizing sequences include, e.g., the sequences shown in SEQ ID NOs:40-46. In a preferred variation, the specific target capture binds the GV 16S rRNA target:capture-probe complex to an immobilized probe to form a target:capture-probe:immobilized-probe complex that is separated from the sample and, optionally, washed to remove non-target sample components (see, e.g., U.S. Pat. Nos. 6,110,678; 6,280,952; and 6,534,273; each incorporated by reference herein). In such variations, the capture probe oligomer further comprises a sequence or moiety that binds attaches the capture probe, with its bound target sequence, to an immobilized probe attached to a solid support, thereby permitting the hybridized target nucleic acid to be separated from other sample components.

In more specific embodiments, the capture probe oligomer includes a tail portion (e.g., a 3' tail) that is not complementary to the G, vaginalis 16S rRNA target sequence but that specifically hybridizes to a sequence on the immobilized probe, thereby serving as the moiety allowing the target nucleic acid to be separated from other sample components, such as previously described in, e.g., U.S. Pat. No. 6,110,678, incorporated herein by reference. Any sequence may be used in a tail region, which is generally about 5 to 50 nt long, and preferred embodiments include a substantially homopolymeric tail of about 10 to 40 nt (e.g., $A_{10}$ to $A_{40}$), more preferably about 14 to 33 nt (e.g., $A_{14}$ to $A_{30}$ or $T_3A_{14}$ to $T_3A_{30}$), that bind to a complementary immobilized sequence (e.g., poly-T) attached to a solid support, e.g., a matrix or particle. For example, in specific embodiments of a capture probe comprising a 3' tail, the capture probe has a sequence selected from SEQ ID NOs: 25-31.

Target capture typically occurs in a solution phase mixture that contains one or more capture probe oligomers that hybridize specifically to the 16S rRNA of G. vaginalis or gene target sequence under hybridizing conditions, usually at a temperature higher than the $T_m$ of the tail-sequence:immobilized-probe-sequence duplex. For embodiments comprising a capture probe tail, the GV-16S-rRNA-target:capture-probe complex is captured by adjusting the hybridization conditions so that the capture probe tail hybridizes to the immobilized probe, and the entire complex on the solid support is then separated from other sample components. The support with the attached immobilized-probe:capture-probe:GV-16S-rRNA-target-sequence may be washed one or more times to further remove other sample components. Preferred embodiments use a particulate solid support, such as paramagnetic beads, so that particles with the attached GV-16S-rRNA-target:capture-probe:immobilized-probe complex may be suspended in a washing solution and retrieved from the washing solution, preferably by using magnetic attraction. To limit the number of handling steps, the G. vaginalis 16S rRNA target nucleic acid may be amplified by simply mixing the GV 16S rRNA target sequence in the complex on the support with amplification oligomers and proceeding with amplification steps.

Amplifying a *Gardnerella vaginalis* target sequence utilizes an in vitro amplification reaction using at least two amplification oligomers that flank a target region to be amplified. In particular embodiments, the target region to be amplified substantially corresponds to SEQ ID NO:88 from about nucleotide position 164 to about nucleotide position 205. Particularly suitable amplification oligomer combinations for amplification of these target regions are described herein. Suitable amplification methods include, for example, replicase-mediated amplification, polymerase chain reaction (PCR), ligase chain reaction (LCR), strand-displacement amplification (SDA), and transcription-mediated or transcription-associated amplification (TMA). Such amplification methods are well-known in the art and are readily used in accordance with the methods of the present invention.

For example, some amplification methods that use TMA amplification include the following steps. Briefly, the target nucleic acid that contains the sequence to be amplified is provided as single stranded nucleic acid (e.g., ssRNA or ssDNA). Those skilled in the art will appreciate that conventional melting of double stranded nucleic acid (e.g., dsDNA) may be used to provide single-stranded target nucleic acids. A promoter primer binds specifically to the target nucleic acid at its target sequence and a reverse transcriptase (RT) extends the 3' end of the promoter primer using the target strand as a template to create a cDNA copy of the target sequence strand, resulting in an RNA:DNA duplex. An RNase digests the RNA strand of the RNA:DNA duplex and a second primer binds specifically to its target sequence, which is located on the cDNA strand downstream from the promoter primer end. RT synthesizes a new DNA strand by extending the 3' end of the second primer using the first cDNA template to create a dsDNA that contains a functional promoter sequence. An RNA polymerase specific for the promoter sequence then initiates transcription to produce RNA transcripts that are about 100 to 1000 amplified copies ("amplicons") of the initial target strand in the reaction. Amplification continues when the second primer binds specifically to its target sequence in each of the amplicons and RT creates a DNA copy from the amplicon RNA template to produce an RNA:DNA duplex. RNase in the reaction mixture digests the amplicon RNA from the RNA:DNA duplex and the promoter primer binds specifically to its complementary sequence in the newly synthesized DNA. RT extends the 3' end of the promoter primer to create a dsDNA that contains a functional promoter to which the RNA polymerase binds to transcribe additional amplicons that are complementary to the target strand. The autocatalytic cycles of making more amplicon copies repeat during the course of the reaction resulting in about a billion-fold amplification of the target nucleic acid present in the sample. The amplified products may be detected in real-time during amplification, or at the end of the amplification reaction by using a probe that binds specifically to a target sequence contained in the amplified products. Detection of a signal resulting from the bound probes indicates the presence of the target nucleic acid in the sample.

In some embodiments, the method utilizes a "reverse" TMA reaction. In such variations, the initial or "forward" amplification oligomer is a priming oligonucleotide that hybridizes to the target nucleic acid in the vicinity of the 3'-end of the target region. A reverse transcriptase (RT) synthesizes a cDNA strand by extending the 3'-end of the primer using the target nucleic acid as a template. The second or "reverse" amplification oligomer is a promoter primer or promoter provider having a target-hybridizing sequence configure to hybridize to a target-sequence contained within the synthesized cDNA strand. Where the second amplification oligomer is a promoter primer, RT extends the 3' end of the promoter primer using the cDNA strand as a template to create a second, cDNA copy of the target sequence strand, thereby creating a dsDNA that contains a functional promoter sequence. Amplification then continues essentially as described above for initiation of transcription from the promoter sequence utilizing an RNA polymerase. Alternatively, where the second amplification oligomer is a promoter provider, a terminating oligonucleotide, which hybridizes to a target sequence that is in the vicinity to the 5'-end of the target region, is typically utilized to terminate extension of the priming oligomer at the 3'-end of the terminating oligonucleotide, thereby providing a defined 3'-end for the initial cDNA strand synthesized by extension from the priming oligomer. The target-hybridizing sequence of the promoter provider then hybridizes to the defined 3'-end of the initial cDNA strand, and the 3'-end of the cDNA strand is extended to add sequence complementary to the promoter sequence of the promoter provider, resulting in the formation of a double-stranded promoter sequence. The initial cDNA strand is then used a template to transcribe multiple RNA transcripts complementary to the initial cDNA strand, not including the promoter portion, using an RNA polymerase that recognizes the double-stranded promoter and initiates transcription therefrom. Each of these RNA transcripts is then available to serve as a template for further amplification from the first priming amplification oligomer.

Detection of the amplified products may be accomplished by a variety of methods. The nucleic acids may be associated with a surface that results in a physical change, such as a detectable electrical change. Amplified nucleic acids may be detected by concentrating them in or on a matrix and detecting the nucleic acids or dyes associated with them (e.g., an intercalating agent such as ethidium bromide or cyber green), or detecting an increase in dye associated with nucleic acid in solution phase. Other methods of detection may use nucleic acid detection probes that are configured to specifically hybridize to a sequence in the amplified product and detecting the presence of the probe:product complex, or by using a complex of probes that may amplify the detectable signal associated with the amplified products (e.g., U.S. Pat. Nos. 5,424,413; 5,451,503; and 5,849,481; each incorporated by reference herein). Directly or indirectly labeled probes that specifically associate with the amplified product provide a detectable signal that indicates the presence of the target nucleic acid in the sample. For example, if the target nucleic acid is the 16S rRNA of *G. vaginalis*, the amplified product will contain a target sequence in or complementary to a sequence in the 16S rRNA of GV, and a probe will bind directly or indirectly to a sequence contained in the amplified product to indicate the presence of the 16S rRNA of GV in the tested sample.

Preferred embodiments of detection probes that hybridize to the complementary amplified sequences may be DNA or RNA oligomers, or oligomers that contain a combination of DNA and RNA nucleotides, or oligomers synthesized with a modified backbone, e.g., an oligomer that includes one or more 2'-methoxy substituted ribonucleotides. Probes used for detection of the amplified *G. vaginalis* rRNA sequences may be unlabeled and detected indirectly (e.g., by binding of another binding partner to a moiety on the probe) or may be labeled with a variety of detectable labels. Particular embodiments of detection probes suitable for use in accordance with methods of the present invention are further described herein. In some preferred embodiments of the method for detecting *G. vaginalis* 16S rRNA sequences, such as in certain embodiments using transcription-mediated amplification (TMA), the detection probe is a linear chemiluminescently labeled probe, more preferably, a linear acridinium ester (AE) labeled probe.

Oligomers that are not intended to be extended by a nucleic acid polymerase preferably include a blocker group that replaces the 3' OH to prevent enzyme-mediated extension of the oligomer in an amplification reaction. For example, blocked amplification oligomers and/or detection probes present during amplification preferably do not have a functional 3' OH and instead include one or more blocking groups located at or near the 3' end. A blocking group near the 3' end is preferably within five residues of the 3' end and is sufficiently large to limit binding of a polymerase to the oligomer, and other preferred embodiments contain a blocking group covalently attached to the 3' terminus. Many different chemical groups may be used to block the 3' end, e.g., alkyl groups, non-nucleotide linkers, alkane-diol dideoxynucleotide residues, and cordycepin.

Examples of oligomers that are typically blocked at the 3' end—and which are particularly suitable in certain embodiments using transcription-mediated amplification—are promoter providers. As described previously, a promoter provider comprises first target-hybridizing region and, situated 5' to the first region, a second region comprising a promoter sequence for an RNA polymerase. The promoter provider oligonucleotide is modified to prevent the initiation of DNA synthesis from its 3'-terminus, such as by including a blocker group as discussed above. In some embodiments, a promoter provider for use in accordance with the detection method comprises a target-hybridizing sequence having a sequence substantially corresponding to, or identical to, a sequence selected from SEQ ID NO:35, SEQ ID NO:36, SEQ ID NO:37, SEQ ID NO:38, and SEQ ID NO:39. In other embodiments, the target-hybridizing of a promoter provider substantially corresponds to, or is identical to, a sequence contained in the sequence of SEQ ID NO:86 and optionally including at least the sequence of SEQ ID NO:85 (e.g., a sequence as shown in SEQ ID NO:36, SEQ ID NO:38, or SEQ ID NO:39). In specific variations, a promoter provider for use in accordance with the detection method has the sequence shown in SEQ ID NO:1, SEQ ID NO:2, SEQ ID NO:3, SEQ ID NO:4, or SEQ ID NO:5.

Another example of typically 3'-blocked oligomers are terminating ("blocker") oligonucleotides, previously described above. A terminating oligomer is typically used in combination with, e.g., a promoter provider amplification oligomer, such as, for example, in certain embodiments described herein relating to transcription-mediated amplification (TMA). A terminating oligomer hybridizes to a sequence contained within the target nucleic acid in the vicinity of the 5'-end of the target region so as to "terminate" primer extension of a nascent nucleic acid that includes a priming oligonucleotide, thereby providing a defined 3'-end for the nascent nucleic acid strand. Particularly suitable terminating oligomers for use in accordance with the present invention have a sequence substantially corresponding to, or identical to, a selected from SEQ ID NO:11, SEQ ID NO:12, SEQ ID NO:13, SEQ ID NO:14, SEQ ID NO:15, and SEQ ID NO:16.

Other embodiments using transcription-mediated amplification utilize a promoter primer, which comprises a first target-hybridizing region and, situated 5' to the first region, a second region comprising a promoter sequence for an RNA polymerase, but which is not modified to prevent the initiation of DNA synthesis from its 3'-terminus. In some embodiments, a promoter primer for use in accordance with the detection method comprises a target-hybridizing sequence having a sequence substantially corresponding to, or identical to, a sequence selected from SEQ ID NO:35, SEQ ID NO:36, SEQ ID NO:37, SEQ ID NO:38, and SEQ ID NO:39. In other embodiments, the target-hybridizing sequence of a promoter primer substantially corresponds to, or is identical to, a sequence contained in the sequence of SEQ ID NO:86 and optionally including at least the sequence of SEQ ID NO:85 (e.g., a sequence as shown in SEQ ID NO:36, SEQ ID NO:38, or SEQ ID NO:39). In specific variations, a promoter primer for use in accordance with the detection method has the sequence shown in SEQ ID NO:1, SEQ ID NO:2, SEQ ID NO:3, SEQ ID NO:4, or SEQ ID NO:5.

Assays for detection of the *G. vaginalis* 16S rRNA nucleic acid may optionally include a non-GV 16S rRNA internal control (IC) nucleic acid that is amplified and detected in the same assay reaction mixtures by using amplification and detection oligomers specific for the IC sequence. IC nucleic acid sequences can be synthetic nucleic acid sequences that are spiked into a sample or the IC nucleic acid sequences may be a cellular component. IC nucleic acid sequences that are cellular components can be from exogenous cellular sources or endogenous cellular sources relative to the specimen. An exogenous cellular source, for example, is a cell that is added into the sample and that then flows through the sample processing procedures along with the specimen. A more particular example would be the addition of a HeLa cell, Jurkat cell, SiLa cell or other to the sample medium along with the specimen that is collected for testing (e.g., a vaginal swab specimen). The specimen and the exogenous cells are then processed, amplified and detected. The specimen being amplified and detected using amplification and detection oligomers for identifying the target sequence of interest and the exogenous cells being amplified and detected using amplification and detection oligomers for identifying an IC target sequence such as 18S rRNA. An endogenous cellular source is a cellular source that would naturally be obtained when gathering the specimen. One example: epithelial cells will present when obtaining a specimen via a vaginal swab. Similar then to the above exemplary exogenous cells process described, the specimen and the endogenous cellular source are both processed, amplified, and detected. The specimen being amplified and detected using amplification and detection oligomers for identifying the target sequence of interest and the endogenous cells being amplified and detected using amplification and detection oligomers for identifying an IC target sequence; typically a housekeeping gene present in the endogenous cellular source, such as a beta-globulin gene. (See e.g., Poljak et al., J. Clin. Virol, 25: S89-97, 2002; U.S. Pat. No. 6,410,321; and US Patent Application Publication No. 2004-0023288; each incorporated by reference herein). Use of a cellular source IC allows for a control from sample collection through detection. Synthetic nucleic acid sequences provide for control of amplification and detection.

In certain embodiments, amplification and detection of a signal from the amplified IC sequence demonstrates that the assay reagents, conditions, and performance of assay steps were properly used in the assay if no signal is obtained for the intended target *G. vaginalis* nucleic acid (e.g., samples that test negative for the 16S rRNA of *G. vaginalis*). An IC may also be used as an internal calibrator for the assay when a quantitative result is desired, i.e., the signal obtained from the IC amplification and detection is used to set a parameter used in an algorithm for quantitating the amount of GV nucleic acid in a sample based on the signal obtained for amplified a GV 16S rRNA target sequence. ICs are also useful for monitoring the integrity of one or more steps in an assay. A preferred embodiment of a synthetic IC nucleic acid sequence is a randomized sequence that has been derived from a naturally occurring source (e.g., an HIV sequence that has been rearranged in a random manner). Another preferred IC nucleic acid sequence may be an RNA transcript isolated from a naturally occurring source or synthesized in vitro, such as by making transcripts from a cloned randomized sequence such that the number of copies of IC included in an assay may be accurately determined. The primers and probe for the IC target sequence are configured and synthesized by using any well-known method provided that the primers and probe function for amplification of the IC target sequence and detection of the amplified IC sequence using substantially the same assay conditions used to amplify and detect the GV target sequence. In preferred embodiments that include a target capture-based purification step, it is preferred that a target capture probe specific for the IC target be included in the assay in the target capture step so that the IC is treated in the assay in a manner analogous to that for the intended GV analyte in all of the assay steps.

Assays for detection of the *G. vaginalis* 16S rRNA nucleic acid may optionally include a pseudotarget. A "pseudotarget" is an oligonucleotide that can be co-amplified with the target polynucleotide in a single amplification reaction. The pseudotarget and target polynucleotide may be amplified using the same set of oligonucleotide primers. The pseudotarget and the target polynucleotide will be non-identical molecules so that the target probe will not detect the pseudotarget.

Amplification methods using pseudotargets are useful for quantifying target polynucleotides present in a test sample. These methods includes steps for: (1) obtaining a test sample that contains an unknown amount of a target polynucleotide; (2) combining a predetermined amount of this test sample with a predetermined amount of a pseudotarget; (3) co-amplifying in an amplification reaction the target polynucleotide and the pseudotarget to produce a collection of amplification products that includes both a target amplicon and a pseudotarget amplicon; and (4) quantifying the target amplicon without relying on information regarding the amount of pseudotarget amplicon produced in the reaction, whereby the quantity of target amplicon is related in a dose-dependent manner to the unknown amount target polynucleotide that was present in the original test sample. Amplification reactions that include a pseudotarget have been shown under certain conditions to provide uniform results having less variability than similar amplification reactions lacking pseudotarget. This is particularly true for amplification of samples containing a low level of target nucleic acid. Using a pseudotarget in an amplification reaction changes the probe RLU output from an all-or-none response to a response wherein the RLU output is proportional to target input. Thus, pseudotarget allows for adjustments in assay sensitivity by changing the cutoff used to classify a sample as positive or negative, rather than re-optimizing the entire amp system to get lower sensitivity through lower amplification efficiency. Pseudotargets are further advantageous for detecting low-levels of target nucleic acid in a specimen. (See also U.S. Pat. No. 6,294,338, incorporated by reference herein).

Detecting *G. vaginalis* to diagnosis bacterial vaginosis in a clinical sample will preferably use higher RLU cut-off values than those used for detecting the presence/absence of GV from a sample. This is because for diagnosis of BV, normal samples can be positive for relatively low amounts of *G. vaginalis* while BV samples will have relatively greater amounts of *G. vaginalis*. So for diagnosis, a higher RLU cut-off value is one approach to differentiating normal levels of GV from elevated levels present in a sample. Depending on the desired application for the amplification and detection oligomers described herein, a skilled artisan will set an appropriate RLU cut-off value, with lower values being useful for detecting all GV present in a sample, and higher RLU values being useful for detecting a threshold amount of GV in a sample.

Additional microbe detection assays can be similarly performed for determining the presence and/or relative amount of a plurality of microbes implicated in BV. By way of example only, such plurality of microbes can include one or more of anaerobic gram-positive cocci; *Atopobium vaginae*; *Lactobacillus* sp.; *Lactobacillus iners*; *Lactobacillus crispatus* group; *Lactobacillus gasseri* group; *Trichomonas* sp.; *Trichomonas vaginalis*; *Candida* sp.; *Eggerthella* sp.; Bacterium from the order Clostridiales; *Clostridium*-like sp.; *Prevotella* sp.; *Prevotella bivia* group; *Prevotella buccalis* group; *Atopobium* sp.; *Atopobium vaginae*; Enterobacteria; *Peptostreptococcus micros*; *Aerococcus christensenii*; *Leptotrichia amnionii*; *Peptoniphilus* sp.; *Dialister* sp.; *Mycoplasma hominis*; *Sneathia sanguinegens*; *Anaerococcus tetradius*; *Mobiluncus* sp.; *Mobiluncus hominis*; *Eggerthella hongkongensis*; *Megasphaera* sp.; *Leptotrichia sanguinegens* and *Finegoldia magna*. Assays may be performed separately or multiplexed. Thus, a diagnosis of BV can include identifying a plurality of microbes and optionally determining their relative abundances in a sample.

Also provided by the subject invention is a reaction mixture for amplification and/or detection of a *Gardnerella vaginalis* target nucleic acid. A reaction mixture in accordance with the present invention at least comprises one or more of the following: an oligomer combination as described herein for amplification of a *G. vaginalis* target nucleic acid; a capture probe oligomer as described herein for purifying the *G. vaginalis* target nucleic acid; a detection probe oligomer as described herein for determining the presence or absence of a *G. vaginalis* amplification product; and a pseudotarget oligomer as described herein for detuning sensitivity of an assay for detecting the *G. vaginalis* target nucleic acid. The reaction mixture may further include a number of optional components such as, for example, arrays of capture probe nucleic acids. For an amplification reaction mixture, the reaction mixture will typically include other reagents suitable for performing in vitro amplification such as, e.g., buffers, salt solutions, appropriate nucleotide triphosphates (e.g., dATP, dCTP, dGTP, dTTP, ATP, CTP, GTP and UTP), and/or enzymes (e.g., reverse transcriptase, and/or RNA polymerase), and will typically include test sample components, in which a *G. vaginalis* target nucleic acid may or may not be present. In addition, for a reaction mixture that includes a detection probe together with an amplification oligomer combination, selection of amplification oligomers and detection probe oligomers for a reaction mixture are linked by a common target region (i.e., the reaction mixture will include a probe that binds to a sequence amplifiable by an amplification oligomer combination of the reaction mixture).

Also provided by the subject invention are kits for practicing the methods as described herein. A kit in accordance with the present invention at least comprises one or more of the following: an amplification oligomer combination as described herein for amplification of a *G. vaginalis* target nucleic acid; a capture probe oligomer as described herein for purifying the *G. vaginalis* target nucleic acid; a detection probe oligomer as described herein for determining the presence or absence of a *G. vaginalis* amplification product; and a pseudotarget oligomer as described herein for detuning sensitivity of an assay for detecting the *G. vaginalis* target nucleic acid. The kits may further include a number of optional components such as, for example, arrays of capture probe nucleic acids. Other reagents that may be present in the kits include reagents suitable for performing in vitro amplification such as, e.g., buffers, salt solutions, appropriate nucleotide triphosphates (e.g., dATP, dCTP, dGTP, dTTP, ATP, CTP, GTP and UTP), and/or enzymes (e.g., reverse transcriptase, and/or RNA polymerase). Oligomers as described herein may be packaged in a variety of different embodiments, and those skilled in the art will appreciate that the invention embraces many different kit configurations. For example, a kit may include amplification oligomers for only one target region of a *G. vaginalis* genome, or it may include amplification oligomers for multiple *G. vaginalis* target regions. In addition, for a kit that includes a detection probe together with an amplification oligomer combination, selection of amplification oligomers and detection probe oligomers for a kit are linked by a common target region (i.e., the kit will include a probe that binds to a sequence amplifiable by an amplification oligomer combination of the kit). In certain embodiments, the kit further includes a set of instructions for practicing methods in accordance with the present invention, where the instructions may be associated with a package insert and/or the packaging of the kit or the components thereof.

The invention is further illustrated by the following non-limiting examples.

Reagents

Various reagents are identified in the examples below, the formulations and pH values (where relevant) of these reagents were as follows.

A "Lysis Buffer" contains 15 mM sodium phosphate monobasic monohydrate, 15 mM sodium phosphate dibasic anhydrous, 1.0 mM EDTA disodium dihydrate, 1.0 mM EGTA free acid, and 110 mM lithium lauryl sulfate, pH 6.7.

A "Target Capture Reagent" contains 250 mM HEPES free acid dihydrate, 310 mM lithium hydroxide monohydrate, 1.88 M lithium chloride, 100 mM EDTA free acid, 2 M lithium hydroxide to pH 6.4, and 250 μg/ml 1 micron magnetic particles Sera-MagTM MG-CM Carboxylate Modified (Seradyn, Inc.; Indianapolis, Ind.; Cat. No. 24152105-050450) having oligo(dT)14 covalently bound thereto.

A "Wash Solution" contains 10 mM HEPES free acid, 6.5 mM sodium hydroxide, 1 mM EDTA free acid, 0.3% (v/v) ethyl alcohol absolute, 0.02% (w/v) methyl paraben, 0.01% (w/v) propyl paraben, 150 mM sodium chloride, 0.1% (w/v) lauryl sulfate, sodium (SDS), and 4 M sodium hydroxide to pH 7.5.

An "Amplification Reagent" is a lyophilized form of a 3.6 mL solution containing 26.7 mM rATP, 5.0 mM rCTP, 33.3 mM rGTP and 5.0 mM rUTP, 125 mM HEPES free acid, 8% (w/v) trehalose dihydrate, 1.33 mM dATP, 1.33 mM dCTP, 1.33 mM dGTP, 1.33 mM dTTP, and 4 M sodium hydroxide to pH 7.5. The Amplification Reagent is reconstituted in 9.7 mL of "Amplification Reagent Reconstitution Solution" described below.

An "Amplification Reagent Reconstitution Solution" contains 0.4% (v/v) ethyl alcohol absolute, 0.10% (w/v) methyl paraben, 0.02% (w/v) propyl paraben, 33 mM KCl, 30.6 mM MgCl2, 0.003% phenol red.

An "Enzyme Reagent" is a lyophilized form of a 1.45 mL solution containing 20 mM HEPES free acid dihydrate, 125 mM N-acetyl-L-cysteine, 0.1 mM EDTA disodium dihydrate, 0.2% (v/v) TRITON® X-100 detergent, 0.2 M trehalose dihydrate, 0.90 RTU/mL Moloney murine leukemia virus ("MMLV") reverse transcriptase, 0.20 U/mL T7 RNA polymerase, and 4M sodium hydroxide to pH 7.0. (One "unit" or "RTU" of activity is defined as the synthesis and release of 5.75 fmol cDNA in 15 minutes at 37 degrees C. for MMLV reverse transcriptase, and for T7 RNA polymerase, one "unit" or "U" of activity is defined as the production of 5.0 fmol RNA transcript in 20 minutes at 37 degrees C.) The Enzyme Reagent is reconstituted in 3.6 mL of "Enzyme Reagent Reconstitution Solution" described below.

An "Enzyme Reagent Reconstitution Solution" contains 50 mM HEPES free acid, 1 mM EDTA free acid, 10% (v/v) TRITON X-100 detergent, 120 mM potassium chloride, 20% (v/v) glycerol anhydrous, and 4 M sodium hydroxide to pH 7.0.

A "Probe Reagent" is a lyophilized form of a 3.6 mL solution containing 110 mM lithium lauryl sulfate, 10 mM of mercaptoethane sulfonic acid, 100 mM lithium succinate, and 3% PVP. The Probe Reagent is reconstituted in 36 mL of "Probe Reagent Reconstitution Solution" described below.

A "Probe Reagent Reconstitution Solution" contains 100 mM succinic acid, 73 mM lithium lauryl sulfate, 100 mM lithium hydroxide monohydrate, 15 mM aldrithiol, 1.2 M lithium chloride, 20 mM EDTA, 3% (v/v) ethyl alcohol, and 2M lithium hydroxide to pH 4.7.

A "Selection Reagent" contains 600 mM boric acid, ACS, 182.5 mM sodium hydroxide, ACS, 1% (v/v) TRITON X-100 detergent, and 4 M sodium hydroxide to pH 8.5.

"Detection Reagents" comprise Detect Reagent I, which contains 1 mM nitric acid and 32 mM hydrogen peroxide, 30% (v/v), and Detect Reagent II, which contains 1.5 M sodium hydroxide.

An "Oil Reagent" is a silicone oil.

Example 1

Reverse TMA (RTMA) T7 Primer Screen for *Gardnerella vaginalis*

The purpose of this experiment was to screen several T7 primers in an RTMA assay with a non-T7 primer, blocker, and probe to identify a set of oligos that amplify with adequate of specificity.

Protocol

The Amplification Reagent was prepared to contain 0.05 pm/microliter of Blocker oligo SEQ ID NO:12, 0.1 pm/microliter of Non-T7 oligo SEQ ID NO:8 and 0.08 pm/microliter of one of the following T7 oligos: SEQ ID NOS:1, 2, 3, 4 or 5. The Probe Reagent was prepared to contain 5E6 RLU/100 microliters of SEQ ID NO:20. Target capture and amplification reactions were prepared and performed as follows: Add 400 ul of 5.0E3 CFU/mL *Gardnerella vaginalis* lysate to each reaction tube. Add 100 ul of Target Capture Reagent ("TCR") reagent with SEQ ID NO:26 at a concentration of 0.05 pm/ul. Incubate in a 60 degree C. Water Bath for 20 minutes. Cool to room temperature for 20 minutes. Place target capture reaction tube onto a magnetic separation device such as the DTS® 400 System (Gen-Probe Incorporated, San Diego, Calif.), for 5 minutes; Aspirate and add 1 mL Wash Solution; Vortex and set back on DTS System for another 5 minutes; and Aspirate again. Add 75 ul of the Amplification Reagent and 200 ul Oil Reagent prepared above to each reaction tube. Incubate 60 degrees C. for 5 minutes in water bath. Cool to 42 degrees C. in water bath for about 5 minutes. Add 25 ul of Enzyme Reagent to each reaction tube, vortex and incubate 42 degrees C. for 60 minutes. Then add 100 ul of the Probe Reagent prepared above to each well; incubate 60 degrees C. for 20 minutes. Add 250 ul of Selection Reagent to each well and incubate 10 minutes at 60 degrees C. Cool to room temperature and read results on a luminometer, such as the LEADER HC luminometer (Gen-Probe Incorporated, San Diego, Calif.), that is capable of injecting 200 ul of Detect Reagent I followed by 200 ul of Detect Reagent II.

Results and Conclusion

TABLE 1

Results for each T7 primer screen with Negative (N = 5) and Positive *Gardnerella vaginalis* lysate

| Amt GV | SEQ ID NO: 1 | SEQ ID NO: 2 | SEQ ID NO: 3 | SEQ ID NO: 4 | SEQ ID NO: 5 |
|---|---|---|---|---|---|
| 0 (Avg RLU) | 5,019,056 | 24,222 | 1,559,159 | 24,240 | 20,957 |
| 0 (±SD) | 3,549,040.1 | 6,047.1 | 1,432,482.5 | 13,224.6 | 866.4 |
| 5e6 CFU/mL (Avg RLU) | 12,130,482 | 12,065,701 | 12,554,996 | 12,124,125 | 802,344 |
| 5e6 CFU/mL (±SD) | 180908 | 392,116.6 | 481,373.1 | 1,000,385.9 | 55,845.1 |

Summary of Results:
1. The results indicated a significant difference in signal to noise with three of the five T7 primers tested in this example.
2. SEQ ID NO:2, SEQ ID NO:4 and SEQ ID NO:5 all had signal to noise ratios of 10-fold or greater.
3. Background signal for SEQ ID NO:5 was in the 20-30K RLU range, using with 5.0E6 RLU/ul of Probe Reagent input.
4. Preferably, the limit of detection ("LOD") for an assay that detects GV to diagnose bacterial vaginosis is set at a high range of ~1.0E6 CFU/mL. several of the above oligomer combinations are useful in such an assay, SEQ ID NO:5 was selected for use in further assays using a high cutoff value with or without a pseudotarget.

Example 2

Probe and Specificity Panel for *Gardnerella vaginalis*

The previous experiment identified several T7 primers that could be used for the detection of GV lysates. The purpose of this next experiment was to identify additional AE-probes, identify probes with the best signal to noise ratio, identify additional non-T7 primers, and perform a specificity screen to detect GV in the presence of *Lactobacillus crispatus, Lactobacillus vaginalis*, and *Bifidobacterium adolescentis*.

Protocol

The Amplification Reagent was prepared generally as described in Example 1, using Blocker oligo SEQ ID NO:12, Non-T7 oligo SEQ ID NO:8 and T7 oligo SEQ ID NO:5. The Probe Reagent was prepared generally as described in Example 1 using one of the following detection probes: SEQ ID NOS:20, 21, 22 or 23. The Amplification Protocol generally followed Example 1.

Results and Conclusion

TABLE 4

Specificity panel *Lactobacillus crispatus*, *Lactobacillus vaginalis*, and *Bifidobacterium asteroids* for SEQ ID NO: 20 detection probe.

| Amt Target | L. crispatus | L. vaginalis | B. asteroids |
|---|---|---|---|
| 0 CFU/mL (Avg/±SD) | 30514.2/1318.2 | 30147.2/387.5 | 31377.4/1044.1 |
| 1e6 CFU/mL (Avg/±SD) | 29849.8/264 | 27011.8/1214.4 | 28938.2/609.2 |

Summary of Results:
1. The results showed that app probes performed well and that the best performing probe in this experiment was SEQ ID NO:22, showing lower background signal.
2. The background signal for SEQ ID NO:22 was 9K RLU vs 17-30K RLU for the other probes.
3. Specificity of the assay against two *Lactobacillus* and one *Bifidobacterium* targets showed no cross reactivity at 1.0E6 CFU/mL.

Example 3

RTMA *Gardnerella vaginalis* Non-T7 Primer Comparison and Probe Specificity Panel The purpose of this experiment was to better characterize the RTMA GV assay. This experiment compared the Non-T7's: SEQ ID NO:8 and SEQ ID NO:7 with T7: SEQ ID NO:5, blocker: SEQ ID NO:12 and probe: SEQ ID NO:22. This experiment also evaluated specificity with the *Lactobacillus vaginalis, Lactobacillus crispatus*, and *Bifidobacterium* panel.

The Amplification Reagent was prepared as is generally described in Example 1 and contained the above mentioned blocker, T7, probe and one of the two Non-T7 oligomers per each separate reaction condition. The Probe Reagent was prepared generally as in Example 1, and the Amplification Protocol was also generally as described in Example 1.

TABLE 3

Probe screening GV assay negative control and 5.0E3 CFU/mL of *Gardnerella vaginalis*

| | SEQ ID NO: 20 | | SEQ ID NO: 21 | | SEQ ID NO: 22 | | SEQ ID NO: 23 | |
|---|---|---|---|---|---|---|---|---|
| Amt GV | Avg (±SD) | % CV | Avg (±SD) | % CV | Avg (±SD) | % CV | Avg (±SD) | % CV |
| 0 | 25,671 (1420.5) | 6 | 18,171 (1576.6) | 9 | 8,761 (363.3) | 4 | 31,135 (1447.8) | 5 |
| 5e3 CFU/mL | 198,077 (17624.3) | 9 | 268,097 (95031) | 35 | 199,346 (48602.7) | 24 | 340,370 (62610) | 18 |

Results and Conclusion

TABLE 5

Comparison of SEQ ID NO: 7 vs SEQ ID NO: 8 with two different concentrations of GV

| Amt GV | SEQ ID NO: 8 | SEQ ID NO: 7 |
|---|---|---|
| 0 CFU/mL | | |
| Avg | 3957.2 | 4477.4 |
| ±SD | 125.4 | 156.6 |
| 5e3 CFU/mL | | |
| Avg | 9346.2 | 537849.4 |
| ±SD | 942.6 | 40534.6 |
| 0 CFU/mL | | |
| Avg | 4525.8 | 4434.8 |
| ±SD | 1103.4 | 120 |
| 5e6 CFU/mL | | |
| Avg | 501499.2 | 9896678 |
| ±SD | 263453.7 | 14557279.7 |

TABLE 6

Specificity panel for RTMA assay system using SEQ ID NO: 22

| Amt Target | L. crispatus | L. vaginalis | B. asteroids |
|---|---|---|---|
| 1e6 CFU/mL | | | |
| Avg | 4451.5 | 4475.6 | 4666.6 |
| SD | 175.6 | 151.6 | 237.3 |

Summary of Results:
1. SEQ ID NO:8 had difficulty in detecting 5.0E3 CFU/mL while SEQ ID NO:7 was capable of detecting from 5.0E3 CFU/mL and up.
2. Depending on the dynamic range of the RTMA assay either non-T7 may be used to help modify the dynamic range of the assay.
3. Specificity appears to be good using SEQ ID NO:7, SEQ ID NO:5, SEQ ID NO12 and SEQ ID NO:22.

Example 4

TMA Amplification and Detection of *G. vaginalis* rRNA

The purpose of this experiment was to screen TMA oligos against the *Gardnerella vaginalis* (GV) rRNA. The experiment compared six different T7 primers with one of non-T7 primer and one probe.

Protocol

The Amplification Reagent was prepared as is generally described in Example 1 to contain, 0.2 pm/microliter of SEQ ID NO:53 as a non-T7 oligo and 0.067 pm/microliter of one of the following T7: SEQ ID NOS:47, 48, 49, 50, 51 or 52. The Probe Reagent was prepared as is generally described in Example 1 and using SEQ ID NO:60. The Amplification Protocol was generally the same as described in Example 1

Results and Conclusion

TABLE 7

T7 primer screening results with negative reaction wells were Sample Transport Media (STM) only and positive reaction wells were 5.0E3 CFU/mL *Gardnerella v.* samples.

| Amt GV | SID: 47 | SID: 48 | SID: 49 | SID: 50 | SID: 51 | SID: 52 |
|---|---|---|---|---|---|---|
| 0 | | | | | | |
| Avg | 976304.2 | 793839.4 | 3092236.2 | 4713453.6 | 4964401.4 | 5504448.2 |
| ±SD | 89595.8 | 134010 | 590582 | 1070413.1 | 407739.6 | 174113 |
| 5e3 CFU/mL | | | | | | |
| Avg | 5443076.8 | 5791614.6 | 6421935.4 | 5939018 | 5333142 | 5354959 |
| ±SD | 90737.4 | 213193.4 | 89854.4 | 98903.7 | 113953.2 | 187094.7 |

SID: stands for SEQ ID NO:

Summary of Results:
1. The results of the experiment showed high background signals with all of the T7 screened with Non-T7: SEQ ID NO:53 and probe: SEQ ID NO:60.
2. One of the best performing T7 primers appears to be the T7: SEQ ID NO:48.

Example 5

*Gardnerella vaginalis* Probe Screening Experiment for Forward TMA Assay

The purpose of this experiment was to screen probes for the forward TMA *G. vaginalis* rRNA assay. This experiment used T7 (SEQ ID NO:47) and non-T7 (SEQ ID NO:53).

Protocol

The Amplification Reagent and the Probe Reagent were prepared as is generally described in Example 4. The Probe Reagent was made to separately contain one of SEQ ID NO:55, 56, 57, 58, 59 or 60. The Amplification Protocol was generally as described in Example 4.

Results and Conclusion

TABLE 8

Results for TMA probe screening of Region 2 *Gardnerella v.* in a Forward TMA amplification system;

| Amt GV | SID: 55 | SID: 56 | SID: 57 | SID: 58 | SID: 59 | SID: 60 |
|---|---|---|---|---|---|---|
| 0 | | | | | | |
| Avg | 3559631.2 | 409615.6 | 6078027.2 | 4486809 | 872283.6 | 535913.2 |
| ±SD | 1173711.3 | 281885.7 | 832413.6 | 683735.5 | 122753.7 | 44781.2 |
| 5e3 CFU/mL | | | | | | |
| Avg | 5205167.2 | 4007322.2 | 9458900.4 | 10689387.4 | 2462665 | 3084617.8 |
| ±SD | 172792.1 | 110206.6 | 165281.7 | 102227.6 | 35947.6 | 434592.4 |

SID: stands for SEQ ID NO:

Summary of Results:
1. The results of the experiment showed the best results with signal to noise to be SEQ ID NO:56 with a negative background of about 190K-900K RLU vs positive signal of about 4E6 RLU/rxn.
2. The result of this experiment suggests that the high negative backgrounds are not due to probe interactions with non-specific target.

Example 6

*Gardnerella vaginalis* TMA Amplification Non-T7 Primer Screen

The purpose of this experiment was to screen non-T7 primers for the forward TMA amplification assay. This study investigated the effect of different non-T7 primers when combined with the previous T7 oligo (SEQ ID NO:47) and Probe oligo (SEQ ID NO:56). This experiment also included some closely related targets: *Lactobacillus vaginalis*, *Crispatus*, and *Bifidobacterium vaginalis*.

Protocol

The Amplification Reagent and the Probe Reagent were prepared as is generally described in Example 4. The Amplification Reagent was made to separately contain one of the following Non-T7 oligos—SEQ ID NOS:61, 62 or 63. The Amplification Protocol was generally as described in Example 4.

Results and Conclusion

TABLE 9

Results for *Gardnerella vaginalis*, non-T7 primer screen with T7 (SEQ ID NO: 47) and probe (SEQ ID NO: 56)

| Amt GV | SEQ ID NO: 63 | SEQ ID NO: 62 | SEQ ID NO: 61 |
|---|---|---|---|
| 0 | | | |
| Avg | 1069184.2 | 301585.8 | 966688.8 |
| ±SD | 1017554.7 | 406667 | 1224516 |
| 5.0E6 CFU/mL | | | |
| Avg | 4259469 | 4080864.4 | 4302645.4 |
| ±SD | 73233.5 | 78340.7 | 112864.6 |

TABLE 10

Specificity panel with T7 (SEQ ID NO: 47), non-T7 (SEQ ID NO: 53) and probe (SEQ ID NO: 56)

| Amt | L. vaginalis | L. crispatus | B. vaginalis |
|---|---|---|---|
| 1E6 CFU/mL | | | |
| Avg | 106966.8 | 391575.4 | 461045.8 |
| ±SD | 104959.0221 | 194672.0411 | 259303.0285 |

Summary of Results:
1. The result of the non-T7 primer screen showed the best non-T7 being SEQ ID NO:62 with background range from about 5K to 1.0E6 RLU/rxn. A high degree of variability was observed with the negative panel suggesting partial amplification.
2. The second experiment showed that background issues are not related to target type but instead to some other type of interaction with oligos or with the STM matrix.

Example 7

*Gardnerella vaginalis* RTMA Specificity Panel

This experiment evaluated the *Gardnerella vaginalis* RTMA assay against a panel of closely related organisms likely to be present in samples tested for bacterial vaginosis (BV). The panel of organisms included: *Atopobium vaginae*, *Bacteroides fragilis*, *Bifidobacterium adolescentis*, *Escherichia coli*, *Fusobacterium nucleatum*, *Gardenerella vaginalis*, *Lactobacillus acidophilus*, *Lactobacillus crispatus*, *Mobiluncus curtisii*, *Prevotella bivia*, *Staphylococcus aureus*, and *Streptococcus agalactiae*. The panel of organisms was tested at 1e6 CFU/mL. The primer set used was the T7: SEQ ID NO:5, Non-T7: SEQ ID NO:8, Blocker: SEQ ID NO:12, and Probe: SEQ ID NO:22. The Amplification Reagent, Probe Reagent and Amplification Protocol were all set-up/performed generally as described in Example 1.

Results and Conclusion

TABLE 11

Results from specificity panel members

| Organism | Avg. | ±SD |
|---|---|---|
| A. vaginae | 5358 | 730.8 |
| B. fragilis | 49028 | 407.3 |
| B. adolescentis | 5440 | 974.9 |
| E. coli | 6326 | 1220.4 |
| F. nucleatum | 6062 | 1150 |
| G. vaginalis | 4569836 | 136461.5 |
| L. acidophilus | 5635 | 901 |
| L. crispatus | 7786 | 2314.3 |
| M. curtisii | 7926 | 1481.6 |
| P. bivia | 7776 | 1513.4 |

TABLE 11-continued

Results from specificity panel members

| Organism | Avg. | ±SD |
|---|---|---|
| S. aureus | 8411 | 4379.5 |
| S. agalactiae | 41816 | 1353.3 |

Summary of Results:
1. The results of this experiment showed little if any amplification with specific organisms, other than *G. vaginalis*.
2. Positive and negative controls were observed to be in acceptable ranges for each condition.
3. Based on this result the current oligo set appears to work well with each panel member at 1.0E6 CFU/mL.

Sequences

TABLE 12

Exemplary Oligomer Sequences, Reference Sequences and Regions

| SEQ ID NO: | Sequence (5' → 3') | Description |
|---|---|---|
| 1 | AATTTAATACGACTCACTATAGGGAGACTGGATGCTCCAACTTGAC | T7 amp oligo |
| 2 | AATTTAATACGACTCACTATAGGGAGAGGATGCTCCAACTTGACGCAT | T7 amp oligo |
| 3 | AATTTAATACGACTCACTATAGGGAGACTGGATGCTCCAACTTGACGC | T7 amp oligo |
| 4 | AATTTAATACGACTCACTATAGGGAGACCAACTTGACGCATGTCTTG | T7 amp oligo |
| 5 | AATTTAATACGACTCACTATAGGGAGACTCCAACTTGACGCATGTCTTGTTGG | T7 amp oligo |
| 6 | CUACAAGCUGAUAGGAC | Non-T7 amp oligo |
| 7 | CCAUTACCCCGCCUACAAG | Non-T7 amp oligo |
| 8 | GUGGGCCAUUACCCCGCCUACAAGC | Non-T7 amp oligo |
| 9 | CUAGGUGGGCCAUUAC | Non-T7 amp oligo |
| 10 | GAAGCCUAGGUGGGCCAUUAC | Non-T7 amp oligo |
| 11 | GUUGGAGCAUCCAGCAUUACCACCCGUUUCC | Blocker |
| 12 | GAGCAUCCAGCAUUACCACCCGUUUC | Blocker |
| 13 | CCAGCAUUACCACCCGUUUCCAAG | Blocker |
| 14 | CAUCCAGCAUUACCACCCGUUUC | Blocker |
| 15 | CAAGUUGGAGCAUCCAGCAUUAC | Blocker |
| 16 | UGCGUCAAGUUGGAGCAUCCAG | Blocker |
| 17 | ACAUGCGUCAAGUUGGAGCAUCCAGC | Blocker |
| 18 | CAAGACAUGCGUCAAGUUGGAGC | Blocker |
| 19 | AACAAGACAUGCGUCAAGUUGGAG | Blocker |
| 20 | CCAUGCCACUAAACACUUUC | Detection probe |
| 21 | CCATGCCACTAAACACTTTC | Detection probe |
| 22 | AUCCCAUGCCACUAAACACUU | Detection probe |
| 23 | CCAUCCCAUGCCACUAAACACUUUC | Detection probe |
| 24 | CAUCCCAUGCCACUAAACAC | Detection probe |

TABLE 12-continued

Exemplary Oligomer Sequences, Reference Sequences and Regions

| SEQ ID NO: | Sequence (5' → 3') | Description |
|---|---|---|
| 25 | CTACTGCTGCCTCCCGTAGGAGTTTAA AAAAAAAAAAAAAA | Target capture oligo |
| 26 | GGACTACCAGGGTATCTAATCCTGTTT AAAAAAA | Target capture oligo |
| 27 | GCAGGUUGGUCACGCAUUACTTT | Target capture oligo |
| 28 | CAUGGGGCAGGUUGGUCACTTT | Target capture oligo |
| 29 | CUCUCAGGCCGGCUACTTT AAAAAAA | Target capture oligo |
| 30 | GGCCGUCCGCCCUCUCAGGCCGTTTAA AAAAAAA | Target capture oligo |
| 31 | CUCAGUCCCAAUGUGGCCGUCTTT AAAAAAA | Target capture oligo |
| 32 | TGCGTACAGAACAACCTGGTGAATTTT GTAGCGTTCACCTCGAA | Pseudotarget |
| 33 | TGCGTACAGAACAACCTTCGAACATCC GCCCCATTACCGGGTG | Pseudotarget |
| 34 | CCATTACCCCGCCTACAAGCCCAACAA GACATGCGTCAAGTTG | Pseudotarget |
| 35 | CTGGATGCTCCAACTTGAC | Target hybridizing sequence (THS) of SEQ ID NO: 1 |
| 36 | GGATGCTCCAACTTGACGCATG | Target hybridizing sequence (THS) of SEQ ID NO: 2 |
| 37 | CTGGATGCTCCAACTTGACGC | Target hybridizing sequence (THS) of SEQ ID NO: 3 |
| 38 | CCAACTTGACGCATGTCTTG | Target hybridizing sequence (THS) of SEQ ID NO: 4 |
| 39 | CTCCAACTTGACGCATGTCTTGTTGG | Target hybridizing sequence (THS) of SEQ ID NO: 5 |
| 40 | CTACTGCTGCCTCCCGTAGGAG | Target hybridizing sequence (THS) of SEQ ID NO: 25 |
| 41 | TCGGACTACCAGGGTATCTAATCCTG | Target hybridizing sequence (THS) of SEQ ID NO: 26 |
| 42 | GCAGGUUGGUCACGCAUUAC | Target hybridizing sequence (THS) of SEQ ID NO: 27 |
| 43 | CAUGGGGCAGGUUGGUCAC | Target hybridizing sequence (THS) of SEQ ID NO: 28 |
| 44 | CUCUCAGGCCGGCUAC | Target hybridizing sequence (THS) of SEQ ID NO: 29 |
| 45 | GGCCGUCCGCCCUCUCAGGCCG | Target hybridizing sequence (THS) of SEQ ID NO: 30 |
| 46 | CUCAGUCCCAAUGUGGCCGUC | Target hybridizing sequence (THS) of SEQ ID NO: 31 |
| 47 | AATTTAATACGACTCACTATAGGGAGA CGAAGGCCTTCATCCCGCACG | T7 amp oligo |
| 48 | AATTTAATACGACTCACTATAGGGAGA GAAGGCCTTCATCCCGCAC | T7 amp oligo |
| 49 | AATTTAATACGACTCACTATAGGGAGA GTTTACAACCCGAAGGCCTTCATC | T7 amp oligo |

TABLE 12-continued

Exemplary Oligomer Sequences, Reference Sequences and Regions

| SEQ ID NO: | Sequence (5' → 3') | Description |
|---|---|---|
| 50 | AATTTAATACGACTCACTATAGGGAGACAAAAGCGGTTTACAACCCGAAG | T7 amp oligo |
| 51 | AATTTAATACGACTCACTATAGGGAGAGCTCCCAATCAAAAGCGGTTTACAAC | T7 amp oligo |
| 52 | AATTTAATACGACTCACTATAGGGAGACTCCCAATCAAAAGCGGTTTAC | T7 amp oligo |
| 53 | CAGTGGGGAATATTGCGCAATG | Non-T7 amp oligo |
| 54 | GGAAACCCUGACGCAGCGAC | Detection probe |
| 55 | GGGGAAACCCUGACGCAG | Detection probe |
| 56 | GGGAAACCCUGACGCAGC | Detection probe |
| 57 | CCCUGACGCAGCGACGCC | Detection probe |
| 58 | UGGGGGAAACCCUGACGCAGCG | Detection probe |
| 59 | GAAACCCUGACGCAGCGACG | Detection probe |
| 60 | GGAAACCCUGACGCAGCGAC | Detection probe |
| 61 | CCTACGGGAGGCAGCAGTGGG | Non-T7 amp oligo |
| 62 | CAGTGGGGAATATTGCGCAATGGG | Non-T7 amp oligo |
| 63 | CAGTGGGGAATATTGCGCAATG | Non-T7 amp oligo |
| 64 | CGAAGGCCTTCATCCCGCACG | Target hybridizing sequence (THS) of SEQ ID NO: 47 |
| 65 | GAAGGCCTTCATCCCGCAC | Target hybridizing sequence (THS) of SEQ ID NO: 48 |
| 66 | GTTTACAACCCGAAGGCCTTCATC | Target hybridizing sequence (THS) of SEQ ID NO: 49 |
| 67 | CAAAAGCGGTTTACAACCCGAAG | Target hybridizing sequence (THS) of SEQ ID NO: 50 |
| 68 | GCTCCCAATCAAAAGCGGTTTACAAC | Target hybridizing sequence (THS) of SEQ ID NO: 51 |
| 69 | CTCCCAATCAAAAGCGGTTTAC | Target hybridizing sequence (THS) of SEQ ID NO: 52 |
| 70 | CCAACTTGAC | Amp oligo core sequence |
| 71 | CTGGATGCTCCAACTTGACGCATGTCTTGTTGG | Amp oligo hybridizing region |
| 72 | CTACAAG | Amp oligo core sequence |
| 73 | CCATTAC | Amp oligo core sequence |
| 74 | GTGGGCCATTAC | Amp oligo core sequence |
| 75 | GAAGCCTAGGTGGGCCATTACCCCGCCTACAAGCTGATAGGAC | Amp oligo hybridizing region |
| 76 | GTGGGCCATTACCCCGCCTACAAGCTGATAGGAC | Amp oligo hybridizing region |
| 77 | CCATTACCCCGCCTACAAG | Amp oligo core sequence |
| 78 | GTGGGCCATTACCCCGCCTACAAGC | Amp oligo hybridizing region |
| 79 | GAAGCCTAGGTGGGCCATTACCCCGCCTACAAGC | Amp oligo hybridizing region |

TABLE 12-continued

Exemplary Oligomer Sequences, Reference Sequences and Regions

| SEQ ID NO: | Sequence (5' → 3') | Description |
|---|---|---|
| 80 | CTAGGTGGGCCATTAC | Amp oligo core sequence |
| 81 | GAAGCCTAGGTGGGCCATTAC | Amp oligo hybridizing region |
| 82 | CCATGCCACTAAACAC | Detection probe core sequence |
| 83 | CCATGCCACTAAACACTT | Detection probe core sequence |
| 84 | CCATCCCATGCCACTAAACACTTTC | Detection probe hybridizing region |
| 85 | CCAACTTGACGCATG | Amp oligo core sequence |
| 86 | GGATGCTCCAACTTGACGCATGTCTTGTTGG | Amp oligo hybridizing region |
| 87 | AATTTAATACGACTCACTATAGGGAGA | T7 promoter sequence |
| 88 | GenBank Accession number EF194095.1 and GI:122938535 (see FIG. 1) | *Gardnerella vaginalis* reference sequence first seen at NCBI on Jan. 23, 2007; entered Feb. 19, 2008; and with non-sequence record updates on Mar. 11, 2010. |

From the foregoing, it will be appreciated that, although specific embodiments of the invention have been described herein for purposes of illustration, various modifications may be made without deviating from the spirit and scope of the invention. Accordingly, the invention is not limited except as by the appended claims. All publications, patents, and patent applications cited herein are hereby incorporated by reference in their entireties for all purposes.

What is claimed is:

1. A combination of at least two oligomers for detecting in a sample a *Gardnerella vaginalis* (GV) 16S rRNA or a gene encoding the 16S rRNA, the oligomer combination comprising:
   first and second amplification oligomers for amplifying a GV nucleic acid target region corresponding to the GV 16S rRNA or the gene encoding the 16S-rRNA, wherein
   (a) the first amplification oligomer comprises a nucleotide sequence, wherein the nucleotide sequence consists of a first target-hybridizing sequence selected from the group consisting of SEQ ID NO:7 and SEQ ID NO:8, and wherein the first amplification oligomer does not comprise an additional target hybridizing sequence; and
   (b) the second amplification oligomer is a promoter primer or promoter provider and comprises a first region nucleotide sequence and a second region nucleotide sequence, wherein (i) the first region nucleotide sequence consists of a second target-hybridizing sequence selected from the group consisting of SEQ ID NO:36, SEQ ID NO:38, and SEQ ID NO:39, and (ii) the second region nucleotide sequence consists of a promoter sequence located 5' to the second target-hybridizing sequence, and wherein the second amplification oligomer does not comprise an additional target hybridizing sequence.

2. The combination of at least two oligomers as in claim 1, wherein the at least two oligomers are in a kit for amplification of a *Gardnerella vaginalis* target nucleic acid.

3. A method for detecting in a sample a *Gardnerella vaginalis* (GV) target nucleic acid, wherein the target nucleic acid is a GV 16S rRNA or a gene encoding the 16S rRNA, the method comprising:
   (a) contacting a sample, the sample suspected of containing a GV bacterium, with at least two oligomers for amplifying a GV nucleic acid target region corresponding to the target nucleic acid, the oligomer combination comprising
   (i) a first amplification oligomer comprising a nucleotide sequence, wherein the nucleotide sequence consists of a first target-hybridizing sequence selected from the group consisting of SEQ ID NO:7 and SEQ ID NO:8, and wherein the first amplification oligomer does not comprise an additional target hybridizing sequence; and
   (ii) a second amplification oligomer that is a promoter primer or promoter provider and that comprises a first region nucleotide sequence and a second region nucleotide sequence, wherein (i) the first region nucleotide sequence consists of a second target-hybridizing sequence selected from the group consisting of SEQ ID NO:36, SEQ ID NO:38, and SEQ ID NO:39, and (ii) the second region nucleotide sequence consists of a promoter sequence located 5' to the second target-hybridizing sequence, and wherein the second amplification oligomer does not comprise a target hybridizing region in addition to the second target hybridizing region;
   (b) performing an in vitro nucleic acid amplification reaction, wherein any GV target nucleic acid present in the sample is used as a template for generating an amplification product; and
   (c) detecting the presence or absence of the amplification product, thereby indicating the presence or absence of GV in the sample.

4. The method of claim 3, wherein the promoter sequence is a T7 promoter sequence has the sequence shown in SEQ ID NO:87.

5. The method of claim 4, wherein the second amplification oligomer comprises a nucleotide sequence that consists of SEQ ID NO:2, SEQ ID NO:4, or SEQ ID NO:5.

6. The method of claim 3, further comprising a step of purifying the GV target nucleic acid from other components in the sample before step (a), wherein the purifying step comprises contacting the sample with at least one capture probe oligomer comprising a target-hybridizing sequence covalently attached to a sequence or moiety that binds to an immobilized probe, wherein the target-hybridizing sequence is selected from the group consisting of SEQ ID NO:40, SEQ ID NO:41, SEQ ID NO:42, SEQ ID NO:43, SEQ ID NO:44, SEQ ID NO:45, and SEQ ID NO:46.

7. The method of claim 3, wherein the detecting step (c) comprises contacting the in vitro nucleic acid amplification reaction with a detection probe oligomer configured to specifically hybridize to the amplification product under conditions whereby the presence or absence of the amplification product is determined, thereby indicating the presence or absence of GV in the sample.

8. The method of claim 7, wherein the detection probe oligomer is selected from the group consisting of:
 a detection probe oligomer comprising a target-hybridizing sequence that is from about 14 to about 35 nucleotides in length and is configured to specifically hybridize to a target sequence contained within SEQ ID NO:88 from about nucleotide position 164 to about nucleotide position 205;
 a detection probe oligomer comprising a target hybridizing sequence contained in the sequence of SEQ ID NO:84 and includes at least the sequence of SEQ ID NO:83; and
 a detection probe oligomer comprising a target hybridizing sequence selected from the group consisting of SEQ ID NO:20, SEQ ID NO:21, SEQ ID NO:22, SEQ ID NO:23, and SEQ ID NO:24.

9. The method of claim 8, wherein the detection probe comprises a label selected from the group consisting of:
 (a) a chemiluminescent label;
 (b) a fluorescent label;
 (c) a quencher; and
 (d) a combination of two or more of (a), (b), and (c).

10. The method of claim 8, wherein the detecting step (c) occurs during the amplifying step (b).

11. The method of claim 8, wherein the detection probe further comprises a non-target-hybridizing sequence.

12. The method of claim 11, wherein the detection probe is a hairpin detection probe a TaqMan detection probe, a molecular beacon, or a molecular torch.

13. The method of claim 3, wherein the amplification reaction at step (b) is an isothermal amplification reaction, or is a PCR amplification reaction.

14. The method of claim 13, wherein the isothermal amplification reaction is a transcription-mediated amplification (TMA) reaction or wherein the isothermal amplification reaction is a reverse TMA reaction.

15. The combination of claim 1, wherein the promoter sequence consists of SEQ ID NO:87.

16. The combination of claim 1, wherein the second amplification oligomer comprises a nucleotide sequence consisting of SEQ ID NO: 2, SEQ ID NO: 4, or SEQ ID NO: 5.

* * * * *

```
                    SEQUENCE LISTING

<160> NUMBER OF SEQ ID NOS: 88

<210> SEQ ID NO 1
<211> LENGTH: 46
<212> TYPE: DNA
<213> ORGANISM: Artificial Sequence
<220> FEATURE:
<223> OTHER INFORMATION: Synthetic Oligomer

<400> SEQUENCE: 1
aatttaatac gactcactat agggagactg gatgctccaa cttgac           46

<210> SEQ ID NO 2
<211> LENGTH: 48
<212> TYPE: DNA
<213> ORGANISM: Artificial Sequence
<220> FEATURE:
<223> OTHER INFORMATION: Synthetic Oligomer

<400> SEQUENCE: 2
aatttaatac gactcactat agggagagga tgctccaact tgacgcat         48

<210> SEQ ID NO 3
<211> LENGTH: 48
<212> TYPE: DNA
<213> ORGANISM: Artificial Sequence
<220> FEATURE:
<223> OTHER INFORMATION: Synthetic Oligomer

<400> SEQUENCE: 3
aatttaatac gactcactat agggagactg gatgctccaa cttgacgc         48
```

<210> SEQ ID NO 4
<211> LENGTH: 47
<212> TYPE: DNA
<213> ORGANISM: Artificial Sequence
<220> FEATURE:
<223> OTHER INFORMATION: Synthetic Oligomer

<400> SEQUENCE: 4
aatttaatac gactcactat agggagacca acttgacgca tgtcttg        47

<210> SEQ ID NO 5
<211> LENGTH: 53
<212> TYPE: DNA
<213> ORGANISM: Artificial Sequence
<220> FEATURE:
<223> OTHER INFORMATION: Synthetic Oligomer

<400> SEQUENCE: 5
aatttaatac gactcactat agggagactc caacttgacg catgtcttgt tgg    53

<210> SEQ ID NO 6
<211> LENGTH: 17
<212> TYPE: DNA
<213> ORGANISM: Artificial Sequence
<220> FEATURE:
<223> OTHER INFORMATION: Synthetic Oligomer

<400> SEQUENCE: 6
cuacaagctg ataggac        17

<210> SEQ ID NO 7
<211> LENGTH: 19
<212> TYPE: DNA
<213> ORGANISM: Artificial Sequence
<220> FEATURE:
<223> OTHER INFORMATION: Synthetic Oligomer

<400> SEQUENCE: 7
ccautacccc gcctacaag        19

<210> SEQ ID NO 8
<211> LENGTH: 25
<212> TYPE: DNA
<213> ORGANISM: Artificial Sequence
<220> FEATURE:
<223> OTHER INFORMATION: Synthetic Oligomer

<400> SEQUENCE: 8
gugggccatt acccgccta caagc        25

<210> SEQ ID NO 9
<211> LENGTH: 16
<212> TYPE: DNA
<213> ORGANISM: Artificial Sequence
<220> FEATURE:
<223> OTHER INFORMATION: Synthetic Oligomer

<400> SEQUENCE: 9
cuaggtgggc cattac        16

<210> SEQ ID NO 10
<211> LENGTH: 21
<212> TYPE: DNA
<213> ORGANISM: Artificial Sequence
<220> FEATURE:
<223> OTHER INFORMATION: Synthetic Oligomer

```
<400> SEQUENCE: 10
gaagcctagg tgggccatta c                                        21

<210> SEQ ID NO 11
<211> LENGTH: 31
<212> TYPE: DNA
<213> ORGANISM: Artificial Sequence
<220> FEATURE:
<223> OTHER INFORMATION: Synthetic Oligomer

<400> SEQUENCE: 11
guuggagcau ccagcauuac cacccguuuc c                             31

<210> SEQ ID NO 12
<211> LENGTH: 26
<212> TYPE: DNA
<213> ORGANISM: Artificial Sequence
<220> FEATURE:
<223> OTHER INFORMATION: Synthetic Oligomer

<400> SEQUENCE: 12
gagcauccag cauuaccacc cguuuc                                   26

<210> SEQ ID NO 13
<211> LENGTH: 24
<212> TYPE: DNA
<213> ORGANISM: Artificial Sequence
<220> FEATURE:
<223> OTHER INFORMATION: Synthetic Oligomer

<400> SEQUENCE: 13
ccagcauuac cacccguuuc caag                                     24

<210> SEQ ID NO 14
<211> LENGTH: 23
<212> TYPE: DNA
<213> ORGANISM: Artificial Sequence
<220> FEATURE:
<223> OTHER INFORMATION: Synthetic Oligomer

<400> SEQUENCE: 14
cauccagcau uaccacccgu uuc                                      23

<210> SEQ ID NO 15
<211> LENGTH: 23
<212> TYPE: DNA
<213> ORGANISM: Artificial Sequence
<220> FEATURE:
<223> OTHER INFORMATION: Synthetic Oligomer

<400> SEQUENCE: 15
caaguuggag cauccagcau uac                                      23

<210> SEQ ID NO 16
<211> LENGTH: 22
<212> TYPE: DNA
<213> ORGANISM: Artificial Sequence
<220> FEATURE:
<223> OTHER INFORMATION: Synthetic Oligomer

<400> SEQUENCE: 16
ugcgucaagu uggagcaucc ag                                       22

<210> SEQ ID NO 17
```

```
<211> LENGTH: 26
<212> TYPE: DNA
<213> ORGANISM: Artificial Sequence
<220> FEATURE:
<223> OTHER INFORMATION: Synthetic Oligomer

<400> SEQUENCE: 17
acaugcguca aguuggagca uccagc                                           26

<210> SEQ ID NO 18
<211> LENGTH: 23
<212> TYPE: DNA
<213> ORGANISM: Artificial Sequence
<220> FEATURE:
<223> OTHER INFORMATION: Synthetic Oligomer

<400> SEQUENCE: 18
caagacaugc gucaaguugg agc                                              23

<210> SEQ ID NO 19
<211> LENGTH: 24
<212> TYPE: DNA
<213> ORGANISM: Artificial Sequence
<220> FEATURE:
<223> OTHER INFORMATION: Synthetic Oligomer

<400> SEQUENCE: 19
aacaagacau gcgucaaguu ggag                                             24

<210> SEQ ID NO 20
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 20
ccaugccacu aaacacuuuc                                                  20

<210> SEQ ID NO 21
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 21
ccatgccact aaacactttc                                                  20

<210> SEQ ID NO 22
<211> LENGTH: 21
<212> TYPE: DNA
<213> ORGANISM: Artificial Sequence
<220> FEATURE:
<223> OTHER INFORMATION: Synthetic Oligomer

<400> SEQUENCE: 22
aucccaugcc acuaaacacu u                                                21

<210> SEQ ID NO 23
<211> LENGTH: 25
<212> TYPE: DNA
<213> ORGANISM: Artificial Sequence
<220> FEATURE:
<223> OTHER INFORMATION: Synthetic Oligomer

<400> SEQUENCE: 23
```

-continued

```
ccaucccaug ccacuaaaca cuuuc                                        25

<210> SEQ ID NO 24
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 24
caucccaugc cacuaaacac                                              20

<210> SEQ ID NO 25
<211> LENGTH: 42
<212> TYPE: DNA
<213> ORGANISM: Artificial Sequence
<220> FEATURE:
<223> OTHER INFORMATION: Synthetic Oligomer

<400> SEQUENCE: 25
ctactgctgc ctcccgtagg agtttaaaaa aaaaaaaaaa aa                     42

<210> SEQ ID NO 26
<211> LENGTH: 57
<212> TYPE: DNA
<213> ORGANISM: Artificial Sequence
<220> FEATURE:
<223> OTHER INFORMATION: Synthetic Oligomer

<400> SEQUENCE: 26
ggactaccag ggtatctaat cctgtttaaa aaaaaaaaaa aaaaaaaaaa aaaaaaa     57

<210> SEQ ID NO 27
<211> LENGTH: 53
<212> TYPE: DNA
<213> ORGANISM: Artificial Sequence
<220> FEATURE:
<223> OTHER INFORMATION: Synthetic Oligomer

<400> SEQUENCE: 27
gcagguuggu cacgcauuac tttaaaaaaa aaaaaaaaaa aaaaaaaaaa aaa         53

<210> SEQ ID NO 28
<211> LENGTH: 52
<212> TYPE: DNA
<213> ORGANISM: Artificial Sequence
<220> FEATURE:
<223> OTHER INFORMATION: Synthetic Oligomer

<400> SEQUENCE: 28 caugggcag guuggucact ttaaaaaaaa aaaaaaaaaa aaaaaaaaaa aa           52

<210> SEQ ID NO 29
<211> LENGTH: 41
<212> TYPE: DNA
<213> ORGANISM: Artificial Sequence
<220> FEATURE:
<223> OTHER INFORMATION: Synthetic Oligomer

<400> SEQUENCE: 29
cucucaggcc ggcuacttta aaaaaaaaaa aaaaaaaaa a                       41

<210> SEQ ID NO 30
<211> LENGTH: 55
<212> TYPE: DNA
```

```
<213> ORGANISM: Artificial Sequence
<220> FEATURE:
<223> OTHER INFORMATION: Synthetic Oligomer

<400> SEQUENCE: 30
ggccguccgc ccucucaggc cgtttaaaaa aaaaaaaaaa aaaaaaaaaa aaaaa          55

<210> SEQ ID NO 31
<211> LENGTH: 41
<212> TYPE: DNA
<213> ORGANISM: Artificial Sequence
<220> FEATURE:
<223> OTHER INFORMATION: Synthetic Oligomer

<400> SEQUENCE: 31
cucaguccca auguggccgu ctttaaaaaa aaaaaaaaaa a                          41

<210> SEQ ID NO 32
<211> LENGTH: 44
<212> TYPE: DNA
<213> ORGANISM: Artificial Sequence
<220> FEATURE:
<223> OTHER INFORMATION: Synthetic Oligomer

<400> SEQUENCE: 32
tgcgtacaga acaacctggt gaattttgta gcgttcacct cgaa                      44

<210> SEQ ID NO 33
<211> LENGTH: 43
<212> TYPE: DNA
<213> ORGANISM: Artificial Sequence
<220> FEATURE:
<223> OTHER INFORMATION: Synthetic Oligomer

<400> SEQUENCE: 33
tgcgtacaga acaaccttcg aacatccgcc ccattaccgg gtg                       43

<210> SEQ ID NO 34
<211> LENGTH: 43
<212> TYPE: DNA
<213> ORGANISM: Artificial Sequence
<220> FEATURE:
<223> OTHER INFORMATION: Synthetic Oligomer

<400> SEQUENCE: 34
ccattacccc gcctacaagc ccaacaagac atgcgtcaag ttg                       43

<210> SEQ ID NO 35
<211> LENGTH: 19
<212> TYPE: DNA
<213> ORGANISM: Artificial Sequence
<220> FEATURE:
<223> OTHER INFORMATION: Synthetic Oligomer

<400> SEQUENCE: 35
ctggatgctc caacttgac                                                  19

<210> SEQ ID NO 36
<211> LENGTH: 22
<212> TYPE: DNA
<213> ORGANISM: Artificial Sequence
<220> FEATURE:
<223> OTHER INFORMATION: Synthetic Oligomer

<400> SEQUENCE: 36
ggatgctcca acttgacgca tg                                              22
```

<210> SEQ ID NO 37
<211> LENGTH: 21
<212> TYPE: DNA
<213> ORGANISM: Artificial Sequence
<220> FEATURE:
<223> OTHER INFORMATION: Synthetic Oligomer

<400> SEQUENCE: 37
ctggatgctc caacttgacg c                                            21

<210> SEQ ID NO 38
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 38
ccaacttgac gcatgtcttg                                              20

<210> SEQ ID NO 39
<211> LENGTH: 26
<212> TYPE: DNA
<213> ORGANISM: Artificial Sequence
<220> FEATURE:
<223> OTHER INFORMATION: Synthetic Oligomer

<400> SEQUENCE: 39
ctccaacttg acgcatgtct tgttgg                                       26

<210> SEQ ID NO 40
<211> LENGTH: 22
<212> TYPE: DNA
<213> ORGANISM: Artificial Sequence
<220> FEATURE:
<223> OTHER INFORMATION: Synthetic Oligomer

<400> SEQUENCE: 40
ctactgctgc ctcccgtagg ag                                           22

<210> SEQ ID NO 41
<211> LENGTH: 26
<212> TYPE: DNA
<213> ORGANISM: Artificial Sequence
<220> FEATURE:
<223> OTHER INFORMATION: Synthetic Oligomer

<400> SEQUENCE: 41
tcggactacc agggtatcta atcctg                                       26

<210> SEQ ID NO 42
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 42
gcagguuggu cacgcauuac                                              20

<210> SEQ ID NO 43
<211> LENGTH: 19
<212> TYPE: DNA
<213> ORGANISM: Artificial Sequence
<220> FEATURE:

```
<223> OTHER INFORMATION: Synthetic Oligomer

<400> SEQUENCE: 43 caugggcag guuggucac                                                    19

<210> SEQ ID NO 44
<211> LENGTH: 16
<212> TYPE: DNA
<213> ORGANISM: Artificial Sequence
<220> FEATURE:
<223> OTHER INFORMATION: Synthetic Oligomer

<400> SEQUENCE: 44
cucucaggcc ggcuac                                                      16

<210> SEQ ID NO 45
<211> LENGTH: 22
<212> TYPE: DNA
<213> ORGANISM: Artificial Sequence
<220> FEATURE:
<223> OTHER INFORMATION: Synthetic Oligomer

<400> SEQUENCE: 45
ggccguccgc ccucucaggc cg                                               22

<210> SEQ ID NO 46
<211> LENGTH: 21
<212> TYPE: DNA
<213> ORGANISM: Artificial Sequence
<220> FEATURE:
<223> OTHER INFORMATION: Synthetic Oligomer

<400> SEQUENCE: 46
cucaguccca auguggccgu c                                                21

<210> SEQ ID NO 47
<211> LENGTH: 48
<212> TYPE: DNA
<213> ORGANISM: Artificial Sequence
<220> FEATURE:
<223> OTHER INFORMATION: Synthetic Oligomer

<400> SEQUENCE: 47
aatttaatac gactcactat agggagacga aggccttcat cccgcacg                   48

<210> SEQ ID NO 48
<211> LENGTH: 46
<212> TYPE: DNA
<213> ORGANISM: Artificial Sequence
<220> FEATURE:
<223> OTHER INFORMATION: Synthetic Oligomer

<400> SEQUENCE: 48
aatttaatac gactcactat agggagagaa ggccttcatc ccgcac                     46

<210> SEQ ID NO 49
<211> LENGTH: 51
<212> TYPE: DNA
<213> ORGANISM: Artificial Sequence
<220> FEATURE:
<223> OTHER INFORMATION: Synthetic Oligomer

<400> SEQUENCE: 49
aatttaatac gactcactat agggagagtt tacaacccga aggccttcat c               51
```

```
<210> SEQ ID NO 50
<211> LENGTH: 50
<212> TYPE: DNA
<213> ORGANISM: Artificial Sequence
<220> FEATURE:
<223> OTHER INFORMATION: Synthetic Oligomer

<400> SEQUENCE: 50
aatttaatac gactcactat agggagacaa aagcggttta caacccgaag            50

<210> SEQ ID NO 51
<211> LENGTH: 53
<212> TYPE: DNA
<213> ORGANISM: Artificial Sequence
<220> FEATURE:
<223> OTHER INFORMATION: Synthetic Oligomer

<400> SEQUENCE: 51
aatttaatac gactcactat agggagagct cccaatcaaa agcggtttac aac         53

<210> SEQ ID NO 52
<211> LENGTH: 49
<212> TYPE: DNA
<213> ORGANISM: Artificial Sequence
<220> FEATURE:
<223> OTHER INFORMATION: Synthetic Oligomer

<400> SEQUENCE: 52
aatttaatac gactcactat agggagactc ccaatcaaaa gcggtttac              49

<210> SEQ ID NO 53
<211> LENGTH: 22
<212> TYPE: DNA
<213> ORGANISM: Artificial Sequence
<220> FEATURE:
<223> OTHER INFORMATION: Synthetic Oligomer

<400> SEQUENCE: 53
cagtggggaa tattgcgcaa tg                                           22

<210> SEQ ID NO 54
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 54
ggaaacccug acgcagcgac                                              20

<210> SEQ ID NO 55
<211> LENGTH: 18
<212> TYPE: DNA
<213> ORGANISM: Artificial Sequence
<220> FEATURE:
<223> OTHER INFORMATION: Synthetic Oligomer

<400> SEQUENCE: 55
ggggaaaccc ugacgcag                                                18

<210> SEQ ID NO 56
<211> LENGTH: 18
<212> TYPE: DNA
<213> ORGANISM: Artificial Sequence
<220> FEATURE:
<223> OTHER INFORMATION: Synthetic Oligomer
```

<400> SEQUENCE: 56
gggaaacccu gacgcagc                                              18

<210> SEQ ID NO 57
<211> LENGTH: 18
<212> TYPE: DNA
<213> ORGANISM: Artificial Sequence
<220> FEATURE:
<223> OTHER INFORMATION: Synthetic Oligomer

<400> SEQUENCE: 57
cccugacgca gcgacgcc                                              18

<210> SEQ ID NO 58
<211> LENGTH: 22
<212> TYPE: DNA
<213> ORGANISM: Artificial Sequence
<220> FEATURE:
<223> OTHER INFORMATION: Synthetic Oligomer

<400> SEQUENCE: 58 uggggggaaac ccugacgcag cg                                         22

<210> SEQ ID NO 59
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 59
gaaacccuga cgcagcgacg                                            20

<210> SEQ ID NO 60
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 60
ggaaacccug acgcagcgac                                            20

<210> SEQ ID NO 61
<211> LENGTH: 21
<212> TYPE: DNA
<213> ORGANISM: Artificial Sequence
<220> FEATURE:
<223> OTHER INFORMATION: Synthetic Oligomer

<400> SEQUENCE: 61
cctacgggag gcagcagtgg g                                          21

<210> SEQ ID NO 62
<211> LENGTH: 24
<212> TYPE: DNA
<213> ORGANISM: Artificial Sequence
<220> FEATURE:
<223> OTHER INFORMATION: Synthetic Oligomer

<400> SEQUENCE: 62
cagtggggaa tattgcgcaa tggg                                       24

<210> SEQ ID NO 63
<211> LENGTH: 22

```
<212> TYPE: DNA
<213> ORGANISM: Artificial Sequence
<220> FEATURE:
<223> OTHER INFORMATION: Synthetic Oligomer

<400> SEQUENCE: 63
cagtggggaa tattgcgcaa tg                                           22

<210> SEQ ID NO 64
<211> LENGTH: 21
<212> TYPE: DNA
<213> ORGANISM: Artificial Sequence
<220> FEATURE:
<223> OTHER INFORMATION: Synthetic Oligomer

<400> SEQUENCE: 64
cgaaggcctt catcccgcac g                                            21

<210> SEQ ID NO 65
<211> LENGTH: 19
<212> TYPE: DNA
<213> ORGANISM: Artificial Sequence
<220> FEATURE:
<223> OTHER INFORMATION: Synthetic Oligomer

<400> SEQUENCE: 65
gaaggccttc atcccgcac                                               19

<210> SEQ ID NO 66
<211> LENGTH: 24
<212> TYPE: DNA
<213> ORGANISM: Artificial Sequence
<220> FEATURE:
<223> OTHER INFORMATION: Synthetic Oligomer

<400> SEQUENCE: 66
gtttacaacc cgaaggcctt catc                                         24

<210> SEQ ID NO 67
<211> LENGTH: 23
<212> TYPE: DNA
<213> ORGANISM: Artificial Sequence
<220> FEATURE:
<223> OTHER INFORMATION: Synthetic Oligomer

<400> SEQUENCE: 67
caaaagcggt ttacaacccg aag                                          23

<210> SEQ ID NO 68
<211> LENGTH: 26
<212> TYPE: DNA
<213> ORGANISM: Artificial Sequence
<220> FEATURE:
<223> OTHER INFORMATION: Synthetic Oligomer

<400> SEQUENCE: 68
gctcccaatc aaaagcggtt tacaac                                       26

<210> SEQ ID NO 69
<211> LENGTH: 22
<212> TYPE: DNA
<213> ORGANISM: Artificial Sequence
<220> FEATURE:
<223> OTHER INFORMATION: Synthetic Oligomer

<400> SEQUENCE: 69
```
ctcccaatca aaagcggttt ac                                              22

<210> SEQ ID NO 70
<211> LENGTH: 10
<212> TYPE: DNA
<213> ORGANISM: Artificial Sequence
<220> FEATURE:
<223> OTHER INFORMATION: Synthetic Oligomer

<400> SEQUENCE: 70
ccaacttgac                                                            10

<210> SEQ ID NO 71
<211> LENGTH: 33
<212> TYPE: DNA
<213> ORGANISM: Artificial Sequence
<220> FEATURE:
<223> OTHER INFORMATION: Synthetic Oligomer

<400> SEQUENCE: 71
ctggatgctc caacttgacg catgtcttgt tgg                                  33

<210> SEQ ID NO 72

<400> SEQUENCE: 72

000

<210> SEQ ID NO 73

<400> SEQUENCE: 73

000

<210> SEQ ID NO 74
<211> LENGTH: 12
<212> TYPE: DNA
<213> ORGANISM: Artificial Sequence
<220> FEATURE:
<223> OTHER INFORMATION: Synthetic Oligomer

<400> SEQUENCE: 74
gtgggccatt ac                                                         12

<210> SEQ ID NO 75
<211> LENGTH: 43
<212> TYPE: DNA
<213> ORGANISM: Artificial Sequence
<220> FEATURE:
<223> OTHER INFORMATION: Synthetic Oligomer

<400> SEQUENCE: 75
gaagcctagg tgggccatta ccccgcctac aagctgatag gac                       43

<210> SEQ ID NO 76
<211> LENGTH: 34
<212> TYPE: DNA
<213> ORGANISM: Artificial Sequence
<220> FEATURE:
<223> OTHER INFORMATION: Synthetic Oligomer

<400> SEQUENCE: 76
gtgggccatt accccgccta caagctgata ggac                                 34

<210> SEQ ID NO 77
<211> LENGTH: 19

<212> TYPE: DNA
<213> ORGANISM: Artificial Sequence
<220> FEATURE:
<223> OTHER INFORMATION: Synthetic Oligomer

<400> SEQUENCE: 77
ccattacccc gcctacaag                                                    19

<210> SEQ ID NO 78
<211> LENGTH: 25
<212> TYPE: DNA
<213> ORGANISM: Artificial Sequence
<220> FEATURE:
<223> OTHER INFORMATION: Synthetic Oligomer

<400> SEQUENCE: 78
gtgggccatt accccgccta caagc                                             25

<210> SEQ ID NO 79
<211> LENGTH: 34
<212> TYPE: DNA
<213> ORGANISM: Artificial Sequence
<220> FEATURE:
<223> OTHER INFORMATION: Synthetic Oligomer

<400> SEQUENCE: 79
gaagcctagg tgggccatta ccccgcctac aagc                                   34

<210> SEQ ID NO 80
<211> LENGTH: 16
<212> TYPE: DNA
<213> ORGANISM: Artificial Sequence
<220> FEATURE:
<223> OTHER INFORMATION: Synthetic Oligomer

<400> SEQUENCE: 80
ctaggtgggc cattac                                                       16

<210> SEQ ID NO 81
<211> LENGTH: 21
<212> TYPE: DNA
<213> ORGANISM: Artificial Sequence
<220> FEATURE:
<223> OTHER INFORMATION: Synthetic Oligomer

<400> SEQUENCE: 81
gaagcctagg tgggccatta c                                                 21

<210> SEQ ID NO 82
<211> LENGTH: 16
<212> TYPE: DNA
<213> ORGANISM: Artificial Sequence
<220> FEATURE:
<223> OTHER INFORMATION: Synthetic Oligomer

<400> SEQUENCE: 82
ccatgccact aaacac                                                       16

<210> SEQ ID NO 83
<211> LENGTH: 18
<212> TYPE: DNA
<213> ORGANISM: Artificial Sequence
<220> FEATURE:
<223> OTHER INFORMATION: Synthetic Oligomer

<400> SEQUENCE: 83

-continued

| | |
|---|---|
| ccatgccact aaacactt | 18 |

<210> SEQ ID NO 84
<211> LENGTH: 25
<212> TYPE: DNA
<213> ORGANISM: Artificial Sequence
<220> FEATURE:
<223> OTHER INFORMATION: Synthetic Oligomer

<400> SEQUENCE: 84

| | |
|---|---|
| ccatcccatg ccactaaaca ctttc | 25 |

<210> SEQ ID NO 85
<211> LENGTH: 15
<212> TYPE: DNA
<213> ORGANISM: Artificial Sequence
<220> FEATURE:
<223> OTHER INFORMATION: Synthetic Oligomer

<400> SEQUENCE: 85

| | |
|---|---|
| ccaacttgac gcatg | 15 |

<210> SEQ ID NO 86
<211> LENGTH: 31
<212> TYPE: DNA
<213> ORGANISM: Artificial Sequence
<220> FEATURE:
<223> OTHER INFORMATION: Synthetic Oligomer

<400> SEQUENCE: 86

| | |
|---|---|
| ggatgctcca acttgacgca tgtcttgttg g | 31 |

<210> SEQ ID NO 87
<211> LENGTH: 27
<212> TYPE: DNA
<213> ORGANISM: Artificial Sequence
<220> FEATURE:
<223> OTHER INFORMATION: Synthetic Oligomer

<400> SEQUENCE: 87

| | |
|---|---|
| aatttaatac gactcactat agggaga | 27 |

<210> SEQ ID NO 88
<211> LENGTH: 1463
<212> TYPE: DNA
<213> ORGANISM: Gardnerella vaginalis
<300> PUBLICATION INFORMATION:
<308> DATABASE ACCESSION NUMBER: EF194095.1 and GI:122938535
<309> DATABASE ENTRY DATE: 2008-02-19
<313> RELEVANT RESIDUES IN SEQ ID NO: (1)..(1463)

<400> SEQUENCE: 88

| | |
|---|---|
| tggcggcgtg cttaacacat gcaagtcgaa cgggatctga ccagcttgct ggttggtgag | 60 |
| agtggcgaac gggtgagtaa tgcgtgacca acctgcccca tgctccagaa tagctcttgg | 120 |
| aaacgggtgg taatgctgga tgctccaact tgacgcatgt cttgtgggga aagtgtttag | 180 |
| tggcatggga tggggtcgcg tcctatcagc ttgtaggcgg ggtaatggcc cacctaggct | 240 |
| tcgacgggta gccggcctga gagggcggac ggccacattg ggactgagat acggcccaga | 300 |
| ctcctacggg aggcagcagt ggggaatatt gcgcaatggg ggaaaccctg acgcagcgac | 360 |
| gccgcgtgcg ggatgaaggc cttcgggttg taaaccgctt ttgattggga gcaagccttt | 420 |
| tgggtgagtg tacctttcga ataagcgccg gctaactacg tgccagcagc cgcggtaata | 480 |
| cgtagggcgc aagcgttatc cggaattatt gggcgtaaag agcttgtagg cggttcgtcg | 540 |

```
cgtctggtgt gaaagcccat cgcttaacgg tgggtttgcg ccgggtacgg gcgggctaga    600
gtgcagtagg ggagactgga attctcggtg taacggtgga atgtgtagat atcgggaaga    660
acaccaatgg cgaaggcagg tctctgggct gttactgacg ctgagaagcg aaagcgtggg    720
gagcgaacag gattagatac cctggtagtc cacgccgtaa acggtggacg ctggatgtgg    780
ggcccattcc acgggttctg tgtcggagct aacgcgttaa gcgtcccgcc tggggagtac    840
ggccgcaagg ctaaaactca aagaaattga cgggggcccg cacaagcggc ggagcatgcg    900
gattaattcg atgcaacgcg aagaacctta cctgggcttg acatgtgcct gacgactgca    960
gagatgtggt ttcctttcgg ggcaggttca caggtggtgc atggtcgtcg tcagctcgtg   1020
tcgtgagatg ttgggttaag tcccgcaacg agcgcaaccc tcgccctgtg ttgccagcgg   1080
gttatgccgg gaactcacgg gggaccgccg gggttaactc ggaggaaggt ggggatgacg   1140
tcagatcatc atgcccctta cgtccagggc ttcacgcatg ctacaatggc cagtacaacg   1200
ggttgyttca tggtgacatg gtgctaatcc cttaaaactg gtctcagttc ggatcgtagt   1260
ctgcaactcg actacgtgaa ggcggagtcg ctagtaatcg cgaatcagca acgtcgcggt   1320
gaatgcgttc ccgggccttg tacacaccgc ccgtcaagtc atgaaagtgg gcagcacccg   1380
aagccggtgg cctaaccctt ttgggatgga gccgtctaag gtgaggctcg tgattgggac   1440
taagtcgtaa caaggtagcc gta                                          1463
```